US008535690B2

(12) United States Patent
Cabezon-Silva et al.

(10) Patent No.: US 8,535,690 B2
(45) Date of Patent: *Sep. 17, 2013

(54) TUMOR SPECIFIC ANIMAL PROTEINS

(75) Inventors: Teresa Elisa Virginia Cabezon-Silva, Rixensart (BE); Jean-Pol Cassart, Rixensart (BE); Thierry Coche, Rixensart (BE); Swann Romain Jean-Thomas Gaulis, Rixensart (BE); Carlota Vinals Y De Bassols, Rixensart (BE)

(73) Assignee: GlaxoSmithKline Biologicals S.A., Rixensart (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/472,035

(22) Filed: May 15, 2012

(65) Prior Publication Data

US 2012/0244175 A1    Sep. 27, 2012

Related U.S. Application Data

(63) Continuation of application No. 12/860,020, filed on Aug. 20, 2010, now Pat. No. 8,207,123, which is a continuation of application No. 11/301,895, filed on Dec. 13, 2005, now Pat. No. 7,803,379, which is a continuation of application No. 10/226,872, filed on Aug. 23, 2002, now abandoned, which is a continuation-in-part of application No. PCT/EP01/01779, filed on Feb. 16, 2001.

(30) Foreign Application Priority Data

Feb. 23, 2000 (GB) .................................. 0004269.7
Apr. 20, 2000 (GB) .................................. 0009905.1
Aug. 25, 2000 (GB) .................................. 0021080.7

(51) Int. Cl.
*A61K 39/00* (2006.01)

(52) U.S. Cl.
USPC .................. 424/277.1; 424/184.1; 424/185.1

(58) Field of Classification Search
None
See application file for complete search history.

(56) References Cited

U.S. PATENT DOCUMENTS

| | | | | |
|---|---|---|---|---|
| 6,087,168 A | * | 7/2000 | Levesque et al. | 435/345 |
| 7,803,379 B2 | * | 9/2010 | Cabezon-Silva et al. | 424/184.1 |
| 8,039,602 B2 | * | 10/2011 | Ryan | 536/23.1 |
| 8,207,123 B2 | * | 6/2012 | Cabezon-Silva et al. | 514/19.3 |
| 2012/0070491 A1 | | 3/2012 | Blais et al. | |

FOREIGN PATENT DOCUMENTS

| WO | 95/17210 | * | 6/1995 |
|---|---|---|---|
| WO | 96/02555 | * | 2/1996 |

OTHER PUBLICATIONS

Campbell, Monoclonal Antibody Technology eds. Elseiver, pp. 1-32, (1984).*
Deutscher, Guide to Protein Purification, vol. 182, Academic Press 1990, pp. 663-670.*
Lipford, Grayson B., (2000); CpG-DNA-Mediated Transient Lymphadenopathy is Associated with a State of Th1 Predisposition to Antigen-Drived Responses, The Journal of Immunology, No. 165; pp. 1228-1235.
Krieg, et al., (2002); CpG Motifs in Bacterial DNA and Their Immune Effects, Annual Rev. Immunology, No. 20; pp. 709-760.
Stills, et al., (2005); Adjuvants and Antibody Production: Dispelling the Myths Associated with Freund's Complete and Other Adjuvants, ILAR Journal; vol. 46; No. 3; pp. 280-293.
Jiang, et al., (2012); USF1 and USF2 Mediate Inhibition of Human Trophoblast Differentiation and CYP19 Gene Expression by Mash-2 and Hypoxia; Molecular and Cellular Biology; No. 23(17); pp. 6117-6128.
Edelman, "An Overview of Adjuvant Use", from Methods in Molecular Medicine, vol. 42, Vaccine Adjuvants: Preparation Methods and Research Protocols, 42:1-27, O'Hagan, ed., Humana Press, Totowa, NJ, 2000.

\* cited by examiner

*Primary Examiner* — Sheela J Huff
(74) *Attorney, Agent, or Firm* — Michael Conger

(57) ABSTRACT

CASB7439 polypeptides and polynucleotides, immunogenic compositions comprising them and methods for producing such polypeptides by recombinant techniques are disclosed. Also disclosed are methods for utilizing CASB7439 polypeptides and polynucleotides in diagnostics, and vaccines for prophylactic and therapeutic treatment of cancers, particularly colorectal cancers, autoimmune diseases, and related conditions.

8 Claims, 8 Drawing Sheets

Figure 3: Coomassie blue stained SDS PAGE of the cell extract from the strain expressing CASB7439

Figure 4: Western blot loaded with cell extract from the strain expressing CASB7439

Figure 5: Coomassie-blue stained SDS-PAGE of CASB7439 after purification

Figure 6: Western blot CASB7439 after purification (monoclonal anti-polyhistidine)

SEQUENCE LISTING

<160> NUMBER OF SEQ ID NOS: 33

<210> SEQ ID NO 1
<211> LENGTH: 1791
<212> TYPE: DNA
<213> ORGANISM: Human

<400> SEQUENCE: 1

| | | | | | |
|---|---|---|---|---|---|
| gtaccttgct | ttgggggcgc | actaagtacc | tgccgggagc | aggggcgca | ccgggaactc | 60 |
| gcagatttcg | ccagttgggc | gcactgggga | tctgtggact | gcgtccgggg | gatgggctag | 120 |
| ggggacatgc | gcacgctttg | ggccttacag | aatgtgatcg | cgcgagggg | agggcgaagc | 180 |
| gtggcgggag | ggcgaggcga | aggaaggagg | gcgtgagaaa | ggcgacggcg | gcggcgcgga | 240 |
| ggagggttat | ctatacattt | aaaaaccagc | cgcctgcgcc | gcgcctgcgg | agacctggga | 300 |
| gagtccggcc | gcacgcgcgg | gacacgagcg | tcccacgctc | cctggcgcgt | acggcctgcc | 360 |
| accactaggc | ctcctatccc | cgggctccag | acgacctagg | acgcgtgccc | tggggagttg | 420 |
| cctggcggcg | ccgtgccaga | agccccttg | gggcgccaca | gttttccccg | tcgcctccgg | 480 |
| ttcctctgcc | tgcaccttcc | tgcggcgcgc | cgggacctgg | agcgggcggg | tggatgcagg | 540 |
| cgcgatggac | ggcggcacac | tgcccaggtc | cgcgccccct | gcgcccccg | tccctgtcgg | 600 |
| ctgcgctgcc | cggcggagac | ccgcgtcccc | ggaactgttg | cgctgcagcc | ggcggcggcg | 660 |
| accggccacc | gcagagaccg | gaggcggcgc | agcggccgta | gcgcggcgca | atgagcgcga | 720 |
| gcgcaaccgc | gtgaagctgg | tgaacttggg | cttccaggcg | ctgcggcagc | acgtgccgca | 780 |
| cggcggcgcc | agcaagaagc | tgagcaaggt | ggagacgctg | cgctcagccg | tggagtacat | 840 |
| ccgcgcgctg | cagcgcctgc | tggccgagca | cgacgccgtg | cgcaacgcgc | tggcgggagg | 900 |
| gctgaggccg | caggccgtgc | ggccgtctgc | gccccgcggg | ccgccaggga | ccaccccggt | 960 |
| cgccgcctcg | ccctcccgcg | cttcttcgtc | ccgggccgc | gggggcagct | cggagcccgg | 1020 |
| ctccccgcgt | tccgcctact | cgtcggacga | cagcggctgc | gaaggcgcgc | tgagtcctgc | 1080 |
| ggagcgcgag | ctactcgact | tctccagctg | gttaggggc | tactgagcgc | cctcgaccta | 1140 |
| tgagcctcag | ccccggaagc | cgagcgagcg | gccggcgcgc | tcatcgccgg | ggagcccgcc | 1200 |
| aggtggaccg | gcccgcgctc | cgcccccagc | gagccgggga | cccacccacc | accccccgca | 1260 |
| ccgccgacgc | cgcctcgttc | gtccggccca | gcctgaccaa | tgccgcggtg | gaaacgggct | 1320 |
| tggagctggc | cccataaggg | ctggcggctt | cctccgacgc | cgcccctccc | cacagcttct | 1380 |
| cgactgcagt | ggggcggggg | gcaccaacac | ttggagattt | ttccggaggg | gagaggattt | 1440 |
| tctaagggca | cagagaatcc | attttctaca | cattaacttg | agctgctgga | gggacactgc | 1500 |
| tggcaaacgg | agacctattt | ttgtacaaag | aacccttgac | ctggggcgta | ataaagatga | 1560 |
| cctggacccc | tgcccccact | atctggagtt | ttccatgctg | gccaagatct | ggacacgagc | 1620 |
| agtccctgag | gggcggggtc | cctggcgtga | ggccccgtg | acagcccacc | ctggggtggg | 1680 |
| tttgtgggca | ctgctgctct | gctagggaga | agcctgtgtg | gggcacacct | cttcaaggga | 1740 |
| gcgtgaactt | tataaataaa | tcagttctgt | ttaaaaaaaa | aaaaaaaaa | a | 1791 |

<210> SEQ ID NO 2
<211> LENGTH: 193
<212> TYPE: PRT
<213> ORGANISM: Human

<400> SEQUENCE: 2

```
Met Asp Gly Gly Thr Leu Pro Arg Ser Ala Pro Ala Pro Pro Val
1               5                   10                  15

Pro Val Gly Cys Ala Ala Arg Arg Arg Pro Ala Ser Pro Glu Leu Leu
            20                  25                  30

Arg Cys Ser Arg Arg Arg Arg Pro Ala Thr Ala Glu Thr Gly Gly Gly
        35                  40                  45

Ala Ala Ala Val Ala Arg Arg Asn Glu Arg Glu Arg Asn Arg Val Lys
    50                  55                  60

Leu Val Asn Leu Gly Phe Gln Ala Leu Arg Gln His Val Pro His Gly
65                  70                  75                  80

Gly Ala Ser Lys Lys Leu Ser Lys Val Glu Thr Leu Arg Ser Ala Val
                85                  90                  95

Glu Tyr Ile Arg Ala Leu Gln Arg Leu Leu Ala Glu His Asp Ala Val
                100                 105                 110

Arg Asn Ala Leu Ala Gly Gly Leu Arg Pro Gln Ala Val Arg Pro Ser
            115                 120                 125

Ala Pro Arg Gly Pro Pro Gly Thr Thr Pro Val Ala Ala Ser Pro Ser
    130                 135                 140

Arg Ala Ser Ser Ser Pro Gly Arg Gly Gly Ser Ser Glu Pro Gly Ser
145                 150                 155                 160

Pro Arg Ser Ala Tyr Ser Ser Asp Asp Ser Gly Cys Glu Gly Ala Leu
                165                 170                 175

Ser Pro Ala Glu Arg Glu Leu Leu Asp Phe Ser Ser Trp Leu Gly Gly
            180                 185                 190

Tyr

<210> SEQ ID NO 3
<211> LENGTH: 262
<212> TYPE: PRT
<213> ORGANISM: Human

<400> SEQUENCE: 3

Met Ser Ala Pro Ala Ala Arg Ser Ala Ser Gly Ala Glu Ala His Arg
1               5                   10                  15

Ser Arg Ala Leu Ser Ser Pro Leu Thr Ser Trp Arg Ser Arg Val Ala
            20                  25                  30

Arg Ala Pro Gln Asp Ser Ala Arg Leu Arg Ser Arg Cys Arg Pro Thr
        35                  40                  45

Ser Arg Arg Asn Ala Gly Ser Arg Ala Pro Ser Cys Pro Arg Gly Pro
    50                  55                  60

Gly Thr Lys Lys Arg Gly Arg Ala Arg Arg Pro Gly Trp Ser Leu
65                  70                  75                  80

Ala Ala Arg Gly Ala Gln Thr Ala Ala Pro Ala Ala Ser Ala Leu
                85                  90                  95

Pro Pro Ala Arg Cys Ala Arg Arg Ala Arg Pro Ala Gly Ala Ala
                100                 105                 110

Ala Arg Gly Cys Thr Pro Arg Leu Ser Ala Ala Ser Pro Pro Cys Ser
            115                 120                 125

Ala Ser Cys Trp Arg Arg Ala Arg Ala Ala Ala Pro Gly
    130                 135                 140

Ser Pro Ser Pro Ala Ser Arg Gly Cys Ala Arg Ala His Cys Ala
145                 150                 155                 160

Ala Leu Arg Pro Leu Arg Arg Leu Arg Ser Leu Arg Trp Pro Val Ala
                165                 170                 175

Ala Ala Gly Cys Ser Ala Thr Val Pro Gly Thr Arg Val Ser Ala Gly
```

```
                    180                 185                 190
Gln Arg Ser Arg Gln Gly Arg Gly Ala Gln Gly Ala Arg Thr Trp Ala
        195                 200                 205

Val Cys Arg Arg Pro Ser Arg Leu His Pro Pro Ala Arg Ser Arg Ser
    210                 215                 220

Arg Arg Ala Ala Gly Arg Cys Arg Gln Arg Asn Arg Arg Arg Gly
225                 230                 235                 240

Lys Leu Trp Arg Pro Lys Gly Ala Ser Gly Thr Ala Pro Pro Gly Asn
                245                 250                 255

Ser Pro Gly His Ala Ser
            260

<210> SEQ ID NO 4
<211> LENGTH: 1830
<212> TYPE: DNA
<213> ORGANISM: Human

<400> SEQUENCE: 4
gtaccttgct ttgggggcgc actaagtacc tgccgggagc aggggggcgca ccgggaactc      60 gcagatttcg ccagttgggc gcactgggga tctgtggact cgtccgggg gatgggctag      120 ggggacatgc gcacgctttg gccttacag aatgtgatcg cgccgagggg gagggccgaa      180
gcgtggcggg agggcgaggc gaaggaagga gggcgtgaga aggcgacgg cggcggcgcg      240 gaggagggtt atctatacat ttaaaaacca gccgcctgcg ccgcgcctgc ggagacctgg      300
gagagtccgg ccgcacgcgc gggacacgag cgtcccacgc tccctggcgc gtacggcctg      360
ccaccactag gcctcctatc cccgggctcc agacgaccta ggacgcgtgc cctggggagt      420
tgcctggcgg cgccgtgcca gaagcccct tgggcgccca cagttttccc cgtcgcctcc      480
ggttcctctg cctgcacctt cctgcggcgc gccgggacct ggagcgggcg gtggatgca      540 ggcgcgatgg acgcggcac actgcccagg tccgcgcccc ctgcgccccc cgtccctgtc      600
ggctgcgctg cccggcggag acccgcgtcc ccggaactgt tgcgctgcag ccggcggcgg      660
cgaccggcca ccgcagagac cggaggcggc gcagcggccg tagcgcggcg caatgagcgc      720
gagcgcaacc gcgtgaagct ggtgaacttg ggcttccagg cgctgcggca gcacgtgccg      780
cacggcggcg ccagcaagaa gctgagcaag gtggagacgc tgcgctcagc cgtggagtac      840
atccgcgcgc tgcagcgcct gctggccgag cacgacgccg tgcgcaacgc gctggcggga      900
gggctgaggc gcaggccgt gcggccgtct cgcccccgcg gccgccagg accaccccg      960 gtcgccgcct cgccctcccg cgcttcttcg tccccgggcc gcggggcag ctcggagccc     1020 ggctcccgc gttccgccta ctcgtcggac acagcggct cgaaggcgc gctgagtcct     1080 gcggagcgcg agctactcga cttctccagc tggttagggg gctactgagc gccctcgacc     1140
taataagcct caagccccgg aaacccgagc gaacgggccg cgcgcttca tcgccgggga     1200 agcccgccaa ggtggaccgg gccgcgctc gccccccagc gagccgggga cccacccacc     1260
accccccgca ccgccgacgc cgcctcgttc gtccggccca gcctgaccaa tgccgcggtg     1320
gaaacgggct tggagctggc cccataaggg ctggcggctt cctccgacgc cgcccctccc     1380
cacagcttct cgactgcagt ggggcggggg gcaccaacac ttggagattt ttccggaggg     1440
gagaggattt tctaagggca cagagaatcc attttctaca cattaacttg agctgctgga     1500
gggacactgc tggcaaacgg agacctattt ttgtacaaag aaacccttgac ctggggcgta     1560 ataaagatga cctggacccc tgcccccact atctggagtt ttccatgctg ccaagatct     1620 ggacacgagc agtccctgag gggcgggtc cctggcgtga ggccccctg acagcccacc     1680
```

```
ctggggtggg tttgtgggca ctgctgctct gctagggaga agcctgtgtg gggcacacct    1740
cttcaaggga gcgtgaactt tataaataaa tcagttctgt ttaaaaaaaa aaaaaaaaa     1800 aaaaccgagg gggggcccgg agccaacaaa                                     1830

<210> SEQ ID NO 5
<211> LENGTH: 587
<212> TYPE: DNA
<213> ORGANISM: Human

<400> SEQUENCE: 5
ggtaaacaga actgatttat ttataaagtt cacgctccct tgaagaggtg tgccccacac      60
aggcttctcc ctagcagagc agcagtgccc acaaacccac cccagggtgg gctgtcacgg     120
gggcctcacg ccagggaccc cgcccctcag ggactgctcg tgtccagatc ttggccagca    180
tggaaaactc cagatagtgg gggcaggggg ccaggtcatc tttattacgc cccaggtcaa    240
gggttctttg tacaaaaata ggtctccgtt tgccagcagt gtccctccag cagctcaagt    300
taatgtgtag aaaatggatt ctctgtgccc ttagaaaatc ctctcccctc cggaaaaatc    360
tccaagtgtt ggtgcccccc gccccactgc agtcgagaag ctgtggggag gggcggcgtc    420
ggaggaagcc gcagcccatt atggggccag ctccaagccc gtttccaccg cggcattggt    480
caggctgggc ggacgaacga ggcggcgtcg gcggtgcggg gggtggtggg tgggtccccg    540
gctcgctggg ggcggagcag cgggccggtc cacctggcgg gctcccc                  587

<210> SEQ ID NO 6
<211> LENGTH: 1791
<212> TYPE: DNA
<213> ORGANISM: Human

<400> SEQUENCE: 6 ttttttttt tttttttta aacagaactg atttatttat aaagttcacg ctcccttgaa       60
gaggtgtgcc ccacacaggc ttctccctag cagagcagca gtgcccacaa acccaccccca   120 gggtgggctg tcacggggc ctcacgccag ggaccccgcc cctcagggac tgctcgtgtc     180
cagatcttgg ccagcatgga aaactccaga tagtgggggc aggggtccag gtcatctttta   240 ttacgcccca ggtcaagggt tctttgtaca aaaataggtc tccgtttgcc agcagtgtcc    300
ctccagcagc tcaagttaat gtgtagaaaa tggattctct gtgcccttag aaaatcctct    360
cccctccgga aaaatctcca agtgttggtg cccccgccc cactgcagtc gagaagctgt     420
ggggaggggc ggcgtcggag gaagccgcca gcccttatgg ggccagctcc aagcccgttt    480
ccaccgcggc attggtcagg ctgggccgga cgaacgaggc ggcgtcggcg gtgcggggggg   540 tggtgggtgg gtccccggct cgctggggc ggagcgcggg ccggtccacc tggcgggctc     600
cccggcgatg agcgcgccgg ccgctcgctc ggcttccggg gctgaggctc ataggtcgag    660
ggcgctcagt agcccctaa ccagctggag aagtcgagta gctcgcgctc gcaggactc      720 agcgcgcctt cgcagccgct gtcgtccgac gagtaggcgg aacgcgggga gccgggctcc    780
gagctgcccc cgcggcccgg ggacgaagaa gcgcggggagg gcgaggcggc gaccggggtg   840
gtccctggcg gcccgcgggg cgcagacggc gcacggcct gcggcctcag ccctcccgcc     900
agcgcgttgc gcaggcgtc gtgctcggcc agcaggcgct gcagcgcgcg gatgtactcc     960
acggtcgagc gcagcgtctc caccttgctc agcttcttgc tggcgccgcc gtgcggcacg   1020
tgctgccgca gcgcctggaa gcccaagttc accagcttca cgcggttgcg ctcgcgctca   1080
ttgcgccgcg ctacggccgc tgcgccgcct ccggtctctg cggtggccgg tcgccgccgc   1140
```

-continued

```
cggctgcagc gcaacagttc cggggacgcg ggtctccgcc gggcagcgca gccgacaggg    1200
acggggggcg caggggggcgc ggacctgggc agtgtgccgc cgtccatcgc gcctgcatcc   1260
acccgcccgc tccaggtccc ggcgcgccgc aggaaggtgc aggcagagga accggaggcg    1320
acggggaaaa ctgtggcgcc caaggggggc ttctggcacg gcgccgccag gcaactcccc    1380
agggcacgcg tcctaggtcg tctggagccc ggggatagga ggcctagtgg tggcaggccg    1440
tacgcgccag ggagcgtggg acgctcgtgt cccgcgcgtg cggccggact ctcccaggtc    1500
tccgcaggcg cggcgcaggc ggctggtttt taaatgtata gataaccctc ctccgcgccg    1560
ccgccgtcgc ctttctcacg ccctccttcc ttcgcctcgc cctcccgcca cgcttcgccc    1620 tcccccctcgc gcgatcacat tctgtaaggc ccaaagcgtg cgcatgtccc cctagcccat   1680
cccccggacg cagtccacag atccccagtg cgcccaactg gcgaaatctg cgagttcccg    1740
gtgcgccccc tgctcccggc aggtacttag tgcgccccca aagcaaggta c             1791
```

<210> SEQ ID NO 7
<211> LENGTH: 361
<212> TYPE: PRT
<213> ORGANISM: Human

<400> SEQUENCE: 7

```
Met Cys Arg Lys Trp Ile Leu Cys Ala Leu Arg Lys Ser Ser Pro Leu
 1               5                  10                  15

Arg Lys Asn Leu Gln Val Leu Pro Pro Ala Pro Leu Gln Ser Arg
            20                  25                  30

Ser Cys Gly Glu Gly Arg Arg Arg Lys Pro Pro Ala Leu Met Gly
        35                  40                  45

Pro Ala Pro Ser Pro Phe Pro Pro Arg His Trp Ser Gly Trp Ala Gly
     50                  55                  60

Arg Thr Arg Arg Arg Arg Cys Gly Gly Trp Trp Val Gly Pro Arg
 65                  70                  75                  80

Leu Ala Gly Gly Gly Ala Arg Ala Arg Ser Thr Leu Ala Gly Phe Pro
                85                  90                  95

Gly Asp Glu Ala Arg Arg Pro Val Arg Ser Gly Phe Arg Gly Leu Arg
            100                 105                 110

Leu Ile Arg Ser Arg Ala Leu Ser Ser Pro Leu Thr Ser Trp Arg Ser
        115                 120                 125

Arg Val Ala Arg Ala Pro Gln Asp Ser Ala Arg Leu Arg Ser Arg Cys
    130                 135                 140

Arg Pro Thr Ser Arg Arg Asn Ala Gly Ser Arg Ala Pro Ser Cys Pro
145                 150                 155                 160

Arg Gly Pro Gly Thr Lys Lys Arg Gly Ala Arg Arg Pro Gly
                165                 170                 175

Trp Ser Leu Ala Ala Arg Gly Ala Gln Thr Ala Ala Arg Pro Ala Ala
            180                 185                 190

Ser Ala Leu Pro Pro Ala Arg Cys Ala Arg Arg Ala Arg Pro Ala
        195                 200                 205

Gly Ala Ala Arg Gly Cys Thr Pro Arg Leu Ser Ala Ala Ser Pro
    210                 215                 220

Pro Cys Ser Ala Ser Cys Trp Arg Arg Ala Ala Arg Ala Ala Ala
225                 230                 235                 240

Ala Pro Gly Ser Pro Ser Ser Pro Ala Ser Arg Gly Cys Ala Arg Ala
                245                 250                 255

His Cys Ala Ala Leu Arg Pro Leu Arg Arg Leu Arg Ser Leu Arg Trp
```

|             |             |             |             |             |             |             |             |             |             |
|-------------|-------------|-------------|-------------|-------------|-------------|-------------|-------------|-------------|-------------|
|             |             | 260         |             |             | 265         |             |             | 270         |             |
| Pro         | Val         | Ala         | Ala         | Ala         | Gly         | Cys         | Ser         | Ala         | Thr         | Val         | Pro         | Gly         | Thr         | Arg         | Val         |
|             |             |             | 275         |             |             |             | 280         |             |             |             | 285         |

Ser Ala Gly Gln Arg Ser Arg Gln Gly Arg Gly Ala Gln Gly Ala Arg
        290                 295                 300

Thr Trp Ala Val Cys Arg Arg Pro Ser Arg Leu His Pro Pro Ala Arg
305                 310                 315                 320

Ser Arg Ser Arg Arg Ala Ala Gly Arg Cys Arg Gln Asn Arg Arg
            325                 330                 335

Arg Arg Gly Lys Leu Trp Arg Pro Lys Gly Ala Ser Gly Thr Ala Pro
        340                 345                 350

Pro Gly Asn Ser Pro Gly His Ala Ser
        355                 360

<210> SEQ ID NO 8
<211> LENGTH: 849
<212> TYPE: DNA
<213> ORGANISM: human

<400> SEQUENCE: 8

```
atggatccaa acactgtgtc aagctttcag gtagattgct ttctttggca tgtccgcaaa      60
cgagttgcag accaagaact aggtgatgcc ccattccttg atcggcttcg ccgagatcag     120
aaatccctaa gaggaagggg cagcaccctc ggtctggaca tcgagacagc cacacgtgct     180
ggaaagcaga tagtggagcg gattctgaaa gaagaatccg atgaggcact taaaatgacc     240
atggacggcg gcacactgcc caggtccgcg ccccctgcgc ccccgtccc tgtcggctgc      300
gctgcccggc ggagacccgc gtccccgaa ctgttgcgct gcagccggcg gcggcgaccg     360
gccaccgcag agaccggagg cggcgcagcg gccgtagcgc ggcgcaatga gcgcgagcgc     420
aaccgcgtga gctggtgaa cttgggcttc caggcgctgc ggcagcacgt gccgcacggc     480
ggcgccagca agaagctgag caaggtggag acgctgcgct cagccgtgga gtacatccgc     540
gcgctgcagc gcctgctggc cgagcacgac gccgtgcgca acgcgctggc gggagggctg    600
aggccgcagg ccgtgcggcc gtctgcgccc cgcgggccgc cagggaccac cccggtcgcc    660
gcctcgccct ccgcgcttc ttcgtccccg ggccgcgggg gcagctcgga gcccggctcc     720
ccgcgttccg cctactcgtc ggacgacagc ggctgcgaag gcgcgctgag tcctgcggag    780
cgcgagctac tcgacttctc cagctggtta gggggctaca ctagtggcca ccatcaccat    840
caccattaa                                                              849
```

<210> SEQ ID NO 9
<211> LENGTH: 849
<212> TYPE: DNA
<213> ORGANISM: human

<400> SEQUENCE: 9

```
atggatccaa acactgtgtc aagctttcag gtagattgct ttctttggca tgtccgcaaa      60
cgagttgcag accaagaact aggtgatgcc ccattccttg atcggcttcg ccgagatcag     120
aaatccctaa gaggaagggg cagcaccctc ggtctggaca tcgagacagc cacacgtgct     180
ggaaagcaga tagtggagcg gattctgaaa gaagaatccg atgaggcact taaaatgacc     240
atggacggcg gcaccctgcc gcgttccgcg ccgccggcgc cgccagttcc ggttggctgc     300
gctgcccgtc gccgtcccgc gtccccgaa ctgctgcgct gcagccgtcg ccgtcgcccg     360
gccaccgcag agaccggagg cggcgcagcg gccgtagcgc ggcgcaatga gcgcgagcgc     420
```

-continued

```
aaccgcgtga agctggtgaa cttgggcttc caggcgctgc ggcagcacgt gccgcacggc    480
ggcgccagca agaagctgag caaggtggag acgctgcgct cagccgtgga gtacatccgc    540
gcgctgcagc gcctgctggc cgagcacgac gccgtgcgca acgcgctggc gggagggctg    600
aggccgcagg ccgtgcggcc gtctgcgccc cgcgggccgc cagggaccac cccggtcgcc    660
gcctcgccct cccgcgcttc ttcgtccccg ggccgcgggg gcagctcgga gcccggctcc    720
ccgcgttccg cctactcgtc ggacgacagc ggctgcgaag gcgcgctgag tcctgcggag    780
cgcgagctac tcgacttctc cagctggtta gggggctaca ctagtggcca ccatcaccat    840
caccattaa                                                            849
```

<210> SEQ ID NO 10
<211> LENGTH: 282
<212> TYPE: PRT
<213> ORGANISM: human

<400> SEQUENCE: 10

```
Met Asp Pro Asn Thr Val Ser Ser Phe Gln Val Asp Cys Phe Leu Trp
  1               5                  10                  15

His Val Arg Lys Arg Val Ala Asp Gln Glu Leu Gly Asp Ala Pro Phe
             20                  25                  30

Leu Asp Arg Leu Arg Arg Asp Gln Lys Ser Leu Arg Gly Arg Gly Ser
         35                  40                  45

Thr Leu Gly Leu Asp Ile Glu Thr Ala Thr Arg Ala Gly Lys Gln Ile
     50                  55                  60

Val Glu Arg Ile Leu Lys Glu Glu Ser Asp Glu Ala Leu Lys Met Thr
 65                  70                  75                  80

Met Asp Gly Gly Thr Leu Pro Arg Ser Ala Pro Ala Pro Pro Pro Val
                 85                  90                  95

Pro Val Gly Cys Ala Ala Arg Arg Pro Ala Ser Pro Glu Leu Leu
            100                 105                 110

Arg Cys Ser Arg Arg Arg Arg Pro Ala Thr Ala Glu Thr Gly Gly Gly
        115                 120                 125

Ala Ala Ala Val Ala Arg Arg Asn Glu Arg Glu Arg Asn Arg Val Lys
    130                 135                 140

Leu Val Asn Leu Gly Phe Gln Ala Leu Arg Gln His Val Pro His Gly
145                 150                 155                 160

Gly Ala Ser Lys Lys Leu Ser Lys Val Glu Thr Leu Arg Ser Ala Val
                165                 170                 175

Glu Tyr Ile Arg Ala Leu Gln Arg Leu Leu Ala Glu His Asp Ala Val
            180                 185                 190

Arg Asn Ala Leu Ala Gly Gly Leu Arg Pro Gln Ala Val Arg Pro Ser
        195                 200                 205

Ala Pro Arg Gly Pro Pro Gly Thr Thr Pro Val Ala Ala Ser Pro Ser
    210                 215                 220

Arg Ala Ser Ser Ser Pro Gly Arg Gly Gly Ser Ser Glu Pro Gly Ser
225                 230                 235                 240

Pro Arg Ser Ala Tyr Ser Ser Asp Asp Ser Gly Cys Glu Gly Ala Leu
                245                 250                 255

Ser Pro Ala Glu Arg Glu Leu Leu Asp Phe Ser Ser Trp Leu Gly Gly
            260                 265                 270

Tyr Thr Ser Gly His His His His His His
        275                 280
```

<210> SEQ ID NO 11

<211> LENGTH: 193
<212> TYPE: PRT
<213> ORGANISM: Human

<400> SEQUENCE: 11

```
Met Tyr Ser Thr Ala Glu Arg Ser Val Ser Thr Leu Leu Ser Phe Leu
  1               5                  10                  15

Leu Ala Pro Pro Cys Gly Thr Cys Cys Arg Ser Ala Trp Lys Pro Lys
             20                  25                  30

Phe Thr Ser Phe Thr Arg Leu Arg Ser Arg Ser Leu Arg Arg Ala Thr
         35                  40                  45

Ala Ala Ala Pro Pro Val Ser Ala Val Ala Gly Arg Arg Arg
     50                  55                  60

Leu Gln Arg Asn Ser Ser Gly Asp Ala Gly Leu Arg Arg Ala Ala Gln
 65                  70                  75                  80

Pro Thr Gly Thr Gly Gly Ala Gly Gly Ala Asp Leu Gly Ser Val Pro
                 85                  90                  95

Pro Ser Ile Ala Pro Ala Ser Thr Arg Pro Leu Gln Val Pro Ala Arg
            100                 105                 110

Arg Arg Lys Val Gln Ala Glu Glu Pro Glu Ala Thr Gly Lys Thr Val
        115                 120                 125

Ala Pro Gln Gly Gly Phe Trp His Gly Ala Ala Arg Gln Leu Pro Arg
    130                 135                 140

Ala Arg Val Leu Gly Arg Leu Glu Pro Gly Asp Arg Arg Pro Ser Gly
145                 150                 155                 160

Gly Arg Pro Tyr Ala Pro Gly Ser Val Gly Arg Ser Cys Pro Ala Arg
                165                 170                 175

Ala Ala Gly Leu Ser Gln Val Ser Ala Gly Ala Ala Gln Ala Ala Gly
            180                 185                 190

Phe
```

<210> SEQ ID NO 12
<211> LENGTH: 263
<212> TYPE: PRT
<213> ORGANISM: Mouse

<400> SEQUENCE: 12

```
Met Glu Ala His Leu Asp Trp Tyr Gly Val Pro Gly Leu Gln Glu Ala
  1               5                  10                  15

Ser Asp Ala Cys Pro Arg Glu Ser Cys Ser Ser Ala Leu Pro Glu Ala
             20                  25                  30

Arg Glu Gly Ala Asn Val His Phe Pro Pro His Pro Val Pro Arg Glu
         35                  40                  45

His Phe Ser Cys Ala Ala Pro Glu Leu Val Ala Gly Ala Gln Gly Leu
     50                  55                  60

Asn Ala Ser Leu Met Asp Gly Gly Ala Leu Pro Arg Leu Met Pro Thr
 65                  70                  75                  80

Ser Ser Gly Val Ala Gly Ala Cys Ala Ala Arg Arg Arg Gln Ala Ser
                 85                  90                  95

Pro Glu Leu Leu Arg Cys Ser Arg Arg Arg Ser Gly Ala Thr Glu
            100                 105                 110

Ala Ser Ser Ser Ala Ala Val Ala Arg Arg Asn Glu Arg Glu Arg
        115                 120                 125

Asn Arg Val Lys Leu Val Asn Leu Gly Phe Gln Ala Leu Arg Gln His
    130                 135                 140

Val Pro His Gly Gly Ala Asn Lys Lys Leu Ser Lys Val Glu Thr Leu
```

```
                145                 150                 155                 160
Arg Ser Ala Val Glu Tyr Ile Arg Ala Leu Gln Arg Leu Leu Ala Glu
                    165                 170                 175

His Asp Ala Val Arg Ala Ala Leu Ala Gly Gly Leu Leu Thr Pro Ala
                    180                 185                 190

Thr Pro Pro Ser Asp Glu Cys Ala Gln Pro Ser Ala Ser Pro Ala Ser
                    195                 200                 205

Ala Ser Leu Ser Cys Ala Ser Thr Ser Pro Ser Pro Asp Arg Leu Gly
                    210                 215                 220

Cys Ser Glu Pro Thr Ser Pro Arg Ser Ala Tyr Ser Ser Glu Glu Ser
225                 230                 235                 240

Ser Cys Glu Gly Glu Leu Ser Pro Met Glu Gln Glu Leu Leu Asp Phe
                    245                 250                 255

Ser Ser Trp Leu Gly Gly Tyr
                    260
```

<210> SEQ ID NO 13
<211> LENGTH: 1051
<212> TYPE: DNA
<213> ORGANISM: Mouse
<220> FEATURE:
<221> NAME/KEY: misc_feature
<222> LOCATION: 810
<223> OTHER INFORMATION: n = A,T,C or G

<400> SEQUENCE: 13

```
gcccggagca tggaagcacg tcagctaggc catgaactgc acccgggagg ggtgggggtg      60
gaagcgcacg gtgtcagctt tgcagaatgt gtacaccaag ggagggcga ggcgaaggaa     120
ggagggcgta agaaaggagg cggtggcggg gcggaggaga ttatctatac tttttaaaaa     180
aaaggagcct cttagccgcg taaaggagac ttggggagcg cctgacagca cgcgcgggac     240
acgagagtac cacgcttccc tactcttttc agaccttgac tggtacgggg tcccaggact     300
gcaggaggcc agcgacgcgt gccctaggga gtcctgcagc agtgccctgc ctgaggcccg     360
tgaaggtgca aacgtccact cccaccgca cccggttcct cgcgagcact tttcctgtgc     420
cgcaccagaa ctcgtagcag gggcccaggg gctgaatgca agcttgatgg acggcggcgc     480
gctgcccaga ctcatgccca cctcgtctgg agtcgctgga gcctgcgctg ctcggcggag     540
acaagcgtct ccggaattgc tgcgctgcag ccggcggcgg cgatctggag caaccgaggc     600
cagcagcagc tcggcgtccg tggcacgccg caatgagcgc gagcgcaacc gcgtaaagct     660
ggtaaacttg ggcttccagg cgctgcggca gcacgtgccg cacggcggcg ccaacaagaa     720
gctgagtaag gtggagacgc tgcgctccgc ggtagagtac attcgtgcgc tgcagcggct     780
gctcgcagag cacgacacgg tgcggccggn gctcgctggg gggctgttaa cacccgctac     840
tccgccgtcc gatgagtgca cgcagccctc tgcctcccct gccagcgggt ctctgtcctg     900
cgcctctacg tctccgtccc ggaccctggg ctgtctgag cctacctccc cgcgctccgc     960
ctactcgtcg gaggaaagca gctgcgaggg agagctaagc ccgatggagc aggagctgct    1020
tgacttttcc agttggttag ggggctactg a                                   1051
```

<210> SEQ ID NO 14
<211> LENGTH: 260
<212> TYPE: PRT
<213> ORGANISM: Rat

<400> SEQUENCE: 14

Met Glu Ser His Phe Asn Trp Tyr Gly Val Pro Arg Leu Gln Lys Ala

```
                1               5              10              15
              Ser Asp Ala Cys Pro Arg Glu Ser Cys Ser Ser Ala Leu Pro Glu Ala
                              20                  25                  30

Arg Glu Gly Ala Asn Val His Phe Pro Pro His Pro Val Pro Arg Glu
                              35                  40                  45

His Phe Ser Cys Gly Ala Pro Lys Pro Val Ala Gly Ala Pro Ala Leu
                              50                  55                  60

Asn Ala Ser Leu Met Asp Gly Gly Ala Leu Pro Arg Leu Val Pro Thr
               65                  70                  75                  80

Ser Ser Gly Val Ala Gly Ala Cys Thr Ala Arg Arg Pro Pro Pro Ser
                              85                  90                  95

Pro Glu Leu Leu Arg Cys Ser Arg Arg Arg Ser Gly Ala Thr Glu
                             100                 105                 110

Ala Ser Ser Ser Ala Ala Val Ala Arg Arg Asn Glu Arg Glu Arg
                             115                 120                 125

Asn Arg Val Lys Leu Val Asn Leu Gly Phe Gln Ala Leu Arg Gln His
                             130                 135                 140

Val Pro His Gly Gly Ala Asn Lys Lys Leu Ser Lys Val Glu Thr Leu
              145                 150                 155                 160

Arg Ser Ala Val Glu Tyr Ile Arg Ala Leu Gln Arg Leu Leu Ala Glu
                             165                 170                 175

His Asp Ala Val Arg Ala Ala Leu Ser Gly Gly Leu Leu Thr Pro Ala
                             180                 185                 190

Thr Arg Pro Ser Asp Val Cys Thr Gln Pro Ser Ala Ser Pro Ala Ser
                             195                 200                 205

Ala Ser Leu Ser Cys Thr Ser Thr Ser Pro Asp Arg Leu Gly Cys Ser
                             210                 215                 220

Glu Pro Ala Ser Pro Arg Ser Ala Tyr Ser Ser Glu Asp Ser Ser Cys
              225                 230                 235                 240

Glu Gly Glu Thr Tyr Pro Met Gly Gln Met Phe Asp Phe Ser Asn Trp
                             245                 250                 255

Leu Gly Gly Tyr
                             260

<210> SEQ ID NO 15
<211> LENGTH: 1526
<212> TYPE: DNA
<213> ORGANISM: Rat

<400> SEQUENCE: 15
ttcacccggc tgcaagcgct aggtgtacgg agacctggca gctcttgggg cttaaggact      60
gagcrccaga gccggtggag gttcctgtgg agtacattcg accctctca  cagccccga     120 gagtgcggga cgtgcggagc gcagttcggg atctgcactc gaggacttgt cgaggacgca    180
ttaagctaag catctgctcg gagcatggaa tcgcacttta actggtacgg ggtcccaagg    240
ctccagaagg ctagcgacgc gtgccctagg gaatcctgca gcagtgccct gcctgaggcc    300
cgtgaaggtg cgaacgtcca cttcccaccg cacccggttc ctcgcgagca cttttcctgt    360
ggcgcaccga aacccgtagc gggggcccg  gcgctgaatg caagcttgat ggacggcggc    420
gcgctgccca gactcgtgcc cacctcgtct ggagtcgctg gagcctgcac tgctcggcgg    480
agacccccgt ccccggaact gcttcgctgc agccgacggc ggcgatcggg agcaaccgag    540
gccagcagca gctcggcggc cgtggcacgc cgcaatgagc gtgagcgcaa ccgcgtaaag    600
ctggtaaact tgggcttcca ggcgctgcgg cagcacgtgc cgcacggcgg cgccaacaag    660
```

```
aagctgagta aggtggagac gctgcgctcc gcggtagagt acatccgtgc gctgcagcgg    720
ctgctagcag agcacgacgc ggtgcgtgct gcgctctctg ggggtctatt aacacccgct    780
actcggccgt ccgatgtgtg cacgcagccc tccgcctccc ctgccagcgc gtctctgtcc    840
tgcacctcta catccccaga ccgcctaggc tgctccgagc ctgcctctcc gcgctccgcc    900
tactcgtcgg aggacagcag ctgcgaggga gagacttacc cgatggggca gatgtttgac    960
ttttccaatt ggttaggggg ctactgagca ccccacaccc ctaagctgcg tccctgggtg   1020
tcccctggtg gacctacctg cgtttcttgc ccaggaaacc tgggcccatg ccttacccat   1080
gctgtctagt gcagcctgac caaatgccaa gtactgacct ctgctcggcc tccacgccgc   1140
ggaatgacat cttccatctc ccagtccttg ccgaaccagg acttggaaat ttctcaggag   1200
aaagaatttt acaatgacaa tctgcttttt atcaattaac ttgaactgct ggaggactct   1260
gctgaaaata tgaagaatta tttttataca aaggatcctt aagcttggag cacaataaag   1320
atgacctctg tctctcaccc ccactgtcta gaactttcca acctggccaa agtgtggacg   1380
ggtcgggccc tgagggcaag atgcctggct gcaccttct tcctcttccg aagcctatcc     1440
tgacgctgat gtttggccag tgtgggaacc ctgctattgc aaagtgtact attctataaa   1500
agttgttttt cattggaaag gaattc                                         1526
```

<210> SEQ ID NO 16
<211> LENGTH: 10
<212> TYPE: PRT
<213> ORGANISM: Human

<400> SEQUENCE: 16

Lys Leu Val Asn Leu Gly Phe Gln Ala Leu
1               5                   10

<210> SEQ ID NO 17
<211> LENGTH: 9
<212> TYPE: PRT
<213> ORGANISM: Human

<400> SEQUENCE: 17

Glu Leu Leu Asp Phe Ser Ser Trp Leu
1               5

<210> SEQ ID NO 18
<211> LENGTH: 9
<212> TYPE: PRT
<213> ORGANISM: Human

<400> SEQUENCE: 18

Arg Leu Leu Ala Glu His Asp Ala Val
1               5

<210> SEQ ID NO 19
<211> LENGTH: 9
<212> TYPE: PRT
<213> ORGANISM: Human

<400> SEQUENCE: 19

Lys Leu Val Asn Leu Gly Phe Gln Ala
1               5

<210> SEQ ID NO 20
<211> LENGTH: 9
<212> TYPE: PRT
<213> ORGANISM: Human

```
<400> SEQUENCE: 20

Glu Tyr Ile Arg Ala Leu Gln Arg Leu
 1               5

<210> SEQ ID NO 21
<211> LENGTH: 10
<212> TYPE: PRT
<213> ORGANISM: Human

<400> SEQUENCE: 21

Glu Tyr Ile Arg Ala Leu Gln Arg Leu Leu
 1               5                  10

<210> SEQ ID NO 22
<211> LENGTH: 10
<212> TYPE: PRT
<213> ORGANISM: Human

<400> SEQUENCE: 22

Ala Val Arg Asn Ala Leu Ala Gly Gly Leu
 1               5                  10

<210> SEQ ID NO 23
<211> LENGTH: 10
<212> TYPE: PRT
<213> ORGANISM: Human

<400> SEQUENCE: 23

Ser Glu Pro Gly Ser Pro Arg Ser Ala Tyr
 1               5                  10

<210> SEQ ID NO 24
<211> LENGTH: 10
<212> TYPE: PRT
<213> ORGANISM: Human

<400> SEQUENCE: 24

Val Glu Thr Leu Arg Ser Ala Val Glu Tyr
 1               5                  10

<210> SEQ ID NO 25
<211> LENGTH: 9
<212> TYPE: PRT
<213> ORGANISM: Human

<400> SEQUENCE: 25

Ile Arg Ala Leu Gln Arg Leu Leu Ala
 1               5

<210> SEQ ID NO 26
<211> LENGTH: 9
<212> TYPE: PRT
<213> ORGANISM: Human

<400> SEQUENCE: 26

Leu Arg Pro Gln Ala Val Arg Pro Ser
 1               5

<210> SEQ ID NO 27
<211> LENGTH: 9
<212> TYPE: PRT
<213> ORGANISM: Protein

<400> SEQUENCE: 27

Leu Arg Gln His Val Pro His Gly Gly
```

```
<210> SEQ ID NO 28
<211> LENGTH: 9
<212> TYPE: PRT
<213> ORGANISM: Human

<400> SEQUENCE: 28

Leu Gly Phe Gln Ala Leu Arg Gln His
 1               5

<210> SEQ ID NO 29
<211> LENGTH: 9
<212> TYPE: PRT
<213> ORGANISM: Human

<400> SEQUENCE: 29

Val Arg Asn Ala Leu Ala Gly Gly Leu
 1               5

<210> SEQ ID NO 30
<211> LENGTH: 9
<212> TYPE: PRT
<213> ORGANISM: Human

<400> SEQUENCE: 30

Tyr Ile Arg Ala Leu Gln Arg Leu Leu
 1               5

<210> SEQ ID NO 31
<211> LENGTH: 9
<212> TYPE: PRT
<213> ORGANISM: Human

<400> SEQUENCE: 31

Leu Val Asn Leu Gly Phe Gln Ala Leu
 1               5

<210> SEQ ID NO 32
<211> LENGTH: 9
<212> TYPE: PRT
<213> ORGANISM: Human

<400> SEQUENCE: 32

Val Glu Tyr Ile Arg Ala Leu Gln Arg
 1               5

<210> SEQ ID NO 33
<211> LENGTH: 9
<212> TYPE: PRT
<213> ORGANISM: Human

<400> SEQUENCE: 33

Leu Leu Arg Cys Ser Arg Arg Arg
 1               5
```

TUMOR SPECIFIC ANIMAL PROTEINS

CROSS REFERENCES TO RELATED APPLICATIONS

This application is a continuation U.S. patent application Ser. No. 12/860,020, filed Aug. 20, 2010, now U.S. Pat. No. 8,207,123, which is a continuation of U.S. patent application Ser. No. 11/301,895 filed Dec. 13, 2005, now issued as U.S. Pat. No. 7,803,379 now abandoned, which is a continuation of U.S. patent application Ser. No. 10/226,872 filed Aug. 23, 2002 now abandoned, which was filed as a continuation-in-part of International Application No. PCT/EP01/01779, filed on Feb. 16, 2001, which claims priority of Great Britain Patent Application No. 0004269.7, filed Feb. 23, 2000, which claims priority of Great Britain Patent Application No. 0009905.1; filed Apr. 20, 2000, which claims priority of Great Britain Patent Application No. 0021080.7, filed Aug. 25, 2000.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

INCORPORATION BY REFERENCE OF MATERIAL SUBMITTED ON A COMPACT DISC

Not applicable.

BACKGROUND OF THE INVENTION

Not applicable.

BRIEF SUMMARY OF THE INVENTION

Not applicable.

BRIEF DESCRIPTION OF THE SEVERAL VIEWS OF THE DRAWING(S)

FIG. 1: shows Real-time PCR data using the Taqman probe. The legend is as follows: Adrenal gland: Ad_Gl; Bladder: Bl; Bone marrow: Bo_Ma; Cervix: Ce; Colon: Co; Fallopian tube: Fa_Tu; Ileon: Il; Liver: Li; Lung: Lu; Lymph node: Ly_No; Oesophagus: Oe; Parathyroid gland: Pa_Thy; Placenta: Pl; Prostate: Pr; Rectum: Re; Skin: Sk; Skeletal muscle: Sk_Mu; Small intestine: Sm_In; Spleen: Sp; Testis: Te; Thyroid gland: Thy; Trachea: Tr.

FIG. 2 shows Real-time PCR expression using Sybr protocol. The legend is as follows: Adrenal gland: Ad_Gl; Bladder: Bl; Bone marrow: Bo_Ma; Cervix: Ce; Colon: Co; Lymph node: Ly_No; Oesophagus: Oe; Parathyroid gland: Pa_Thy; Placenta: Pl; Prostate: Pr; Rectum: Re; Skin: Sk; Skeletal muscle: Sk_Mu; Small intestine: Sm_In; Spleen: Sp; Testis: Te; Thyroid gland: Thy; Trachea: Tr; Heart: He.

FIG. 3 shows Coomassie blue stained SDS PAGE of the cell extract from the strain expressing CASB7439. Lane 1 shows the molecular markers, lane 2 the cellular extract induced 5 h at 39° C.; lane 3 shows the supernatant of cellular extract induced; and lane 4 shows the pellet of cellular extract induced.

FIG. 4 shows a Western blot analysis of NS1-CASB7439 expressed protein. The gel is loaded with the cell extract from the strain expressing CASB7439 and revealed with anti-NS1 monoclonal antibody.

FIG. 5 shows a Coomassie-blue stained SDS-PAGE of CASB7439 after purification. Lanes 1 and 5 represent the molecular weight markers; lanes 2, 3, 4 are respectively loaded with 2 µl, 4 µl and 6 µl of purified protein.

DETAILED DESCRIPTION OF THE INVENTION

Figure 1:
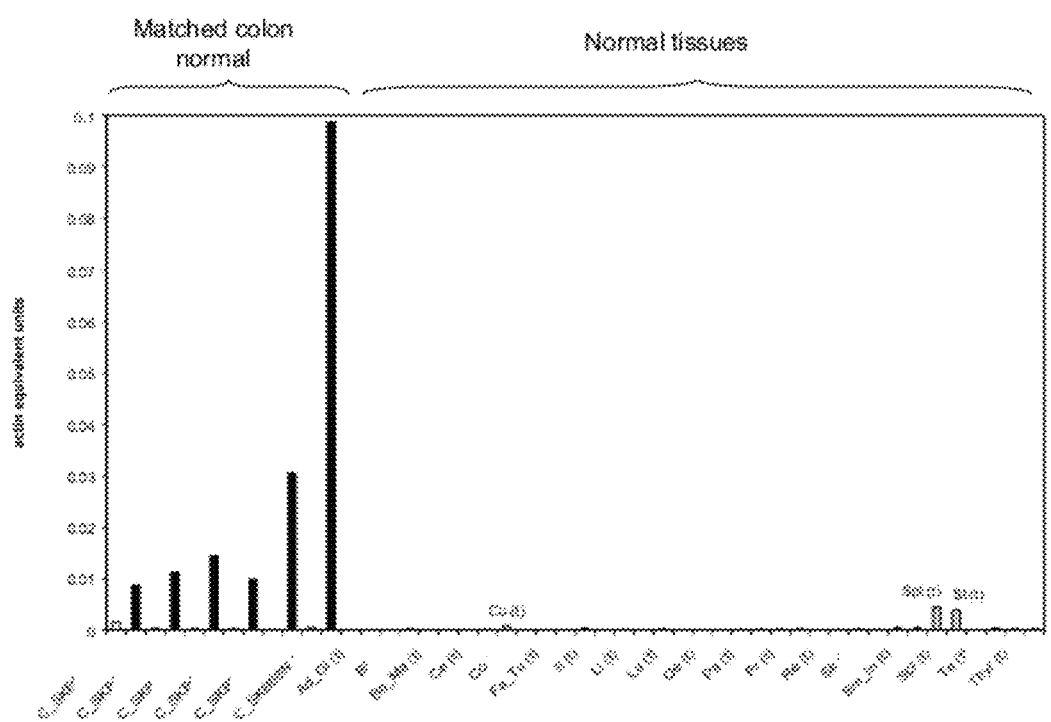

The present invention relates to pharmaceutical compositions and methods for inducing an immune response against tumours-related antigens. More specifically, the invention relates to polynucleotides, herein referred to as CASB7439 polynucleotides, polypeptides encoded thereby (referred to herein as CASB7439 polypeptides), recombinant materials and methods for their production. In another aspect, the invention relates to methods for using such polypeptides and polynucleotides, including the treatment of cancer, more particularly colorectal cancer, and autoimmune diseases and other related conditions. In another aspect, the invention relates to pharmaceutical compositions containing CASB7439 polypeptides and polynucleotides, to methods of manufacture of such compositions and to their use in medicine. In a further aspect, the invention relates to methods for identifying agonists and antagonists/inhibitors using the materials provided by the invention, and treating conditions associated with CASB7439 polypeptide imbalance with the identified compounds. In a still further aspect, the invention relates to diagnostic assays for detecting diseases associated with inappropriate CASB7439 polypeptide activity or levels.

Polypeptides and polynucleotides of the present invention are believed to be important immunogens for specific prophylactic or therapeutic immunization against tumours, because they are specifically expressed or highly over-expressed in tumours compared to normal cells and can thus be targeted by antigen-specific immune mechanisms leading to the destruction of the tumour cell. They can also be used to diagnose the occurrence of tumour cells. Furthermore, their inappropriate expression in certain circumstances can cause an induction of autoimmune, inappropriate immune responses, which could be corrected through appropriate vaccination using the same polypeptides or polynucleotides. In this respect the most important biological activities to our purpose are the antigenic and immunogenic activities of the polypeptide of the present invention. A polypeptide of the present invention may also exhibit at least one other biological activity of a CASB7439 polypeptide, which could qualify it as a target for therapeutic or prophylactic intervention different from that linked to the immune response.

In a first aspect, the present invention relates to CASB7439 polypeptides. Such peptides include isolated polypeptides, comprising an amino acid sequence which has at least 70% identity, preferably at least 80% identity, more preferably at least 90% identity, yet more preferably at least 95% identity, most preferably at least 97-99% identity, to that of SEQ ID NO:2, SEQ ID NO:3, SEQ ID NO:7, SEQ ID NO:10, SEQ ID NO:11, SEQ ID NO:12 or SEQ ID NO:14 over the entire length of SEQ ID NO:2, SEQ ID NO:3, SEQ ID NO:7, SEQ ID NO:10, SEQ ID NO:11, SEQ ID NO:12 or SEQ ID NO:14 respectively, with the proviso that said isolated polypeptide is not SEQ ID NO:2, SEQ ID NO:12 or SEQ ID NO:14. Such polypeptides include those comprising the amino acid of SEQ ID NO:3, SEQ ID NO:7, SEQ ID NO:10 and SEQ ID NO:11.

Further peptides of the present invention include isolated polypeptides, in which the amino acid sequence has at least 70% identity, preferably at least 80% identity, more preferably at least 90% identity, yet more preferably at least 95% identity, most preferably at least 97-99% identity, to the amino acid sequence of SEQ ID NO:2, SEQ ID NO:3, SEQ ID NO:7, SEQ ID NO:10, SEQ ID NO:11, SEQ ID NO:12 or SEQ ID NO:14 over the entire length of SEQ ID NO:2, SEQ ID NO:3, SEQ ID NO:7, SEQ ID NO:10, SEQ ID NO:11, SEQ ID NO:12 or SEQ ID NO:14 respectively, with the proviso that said isolated polypeptide is not SEQ ID NO:2, SEQ ID NO:12 or SEQ ID NO:14. Such polypeptides include the polypeptides of SEQ ID NO:3, SEQ ID NO:7, SEQ ID NO:10 and SEQ ID NO:11.

Preferably the aforementioned polypeptides are recombinantly produced. Most preferably the polypeptides according to the invention are purified, and are substantially free of any other proteins or contaminating host-originating material.

Further peptides of the present invention include isolated polypeptides encoded by a polynucleotide comprising the sequence contained in SEQ ID NO:1.

The invention also provides an immunogenic fragment of a CASB7439 polypeptide, that is a contiguous portion of the CASB7439 polypeptide which has the same or similar immunogenic properties to the polypeptide comprising the amino acid sequence of SEQ ID NO:2, SEQ ID NO:3, SEQ ID NO:7, SEQ ID NO:10, SEQ ID NO:11, SEQ ID NO:12 or SEQ ID NO:14. That is to say, the fragment (if necessary when coupled to a carrier or as part of a larger fusion protein) is capable of raising an immune response which recognises the CASB7439 polypeptide. Such an immunogenic fragment may include, for example, the CASB7439 polypeptide lacking an N-terminal leader sequence, a transmembrane domain or a C-terminal anchor domain. In a preferred aspect the immunogenic fragment of CASB7439 according to the invention comprises substantially all of the extracellular domain of a polypeptide which has at least 70% identity, preferably at least 80% identity, more preferably at least 90% identity, yet more preferably at least 95% identity, most preferably at least 97-99% identity, to that of SEQ ID NO:2, SEQ ID NO:3, SEQ ID NO:7, SEQ ID NO:10, SEQ ID NO:11, SEQ ID NO:12 or SEQ ID NO:14 over the entire length of SEQ ID NO:2, SEQ ID NO:3, SEQ ID NO:7, SEQ ID NO:10, SEQ ID NO:11, SEQ ID NO:12 or SEQ ID NO:14, respectively. Preferably an immunogenic fragment according to the invention comprises at least one epitope.

Peptide fragments incorporating an epitope of CASB7439 typically will comprise at least 7, preferably 9 or 10 contiguous amino acids from SEQ ID NO:2. Preferred epitopes are shown in SEQ ID NO:16 to SEQ ID NO:33.

Peptides that incorporate these epitopes form a preferred aspect of the present invention. Mimotopes which have the same characteristics as these epitopes, and immunogens comprising such mimotopes which generate an immune response which cross-react with an epitope in the context of the CASB7439 molecule, also form part of the present invention.

The present invention, therefore, includes isolated peptides encompassing these epitopes themselves, and any mimotope thereof. The meaning of mimotope is defined as an entity which is sufficiently similar to the native CASB7439 epitope so as to be capable of being recognised by antibodies which recognise the native molecule; (Gheysen, H. M., et al., 1986, Synthetic peptides as antigens. Wiley, Chichester, Ciba foundation symposium 119, p 130-149; Gheysen, H. M., 1986, Molecular Immunology, 23, 7, 709-715); or are capable of raising antibodies, when coupled to a suitable carrier, which antibodies cross-react with the native molecule.

Peptide mimotopes of the above-identified epitopes may be designed for a particular purpose by addition, deletion or substitution of elected amino acids. Thus, the peptides of the present invention may be modified for the purposes of ease of conjugation to a protein carrier. For example, it may be desirable for some chemical conjugation methods to include a terminal cysteine to the epitope. In addition it may be desirable for peptides conjugated to a protein carrier to include a hydrophobic terminus distal from the conjugated terminus of the peptide, such that the free unconjugated end of the peptide remains associated with the surface of the carrier protein. This reduces the conformational degrees of freedom of the peptide, and thus increases the probability that the peptide is presented in a conformation which most closely resembles that of the peptide as found in the context of the whole molecule. For example, the peptides may be altered to have an N-terminal cysteine and a C-terminal hydrophobic amidated tail. Alternatively, the addition or substitution of a D-stereoisomer form of one or more of the amino acids may be performed to create a beneficial derivative, for example to enhance stability of the peptide. Those skilled in the art will realise that such modified peptides, or mimotopes, could be a wholly or partly non-peptide mimotope wherein the constituent residues are not necessarily confined to the 20 naturally occurring amino acids. In addition, these may be cyclised by techniques known in the art to constrain the peptide into a conformation that closely resembles its shape when the peptide sequence is in the context of the whole molecule. A preferred method of cyclising a peptide comprises the addition of a pair of cysteine residues to allow the formation of a disulphide bridge.

Further, those skilled in the art will realise that mimotopes or immunogens of the present invention may be larger than the above-identified epitopes, and as such may comprise the sequences disclosed herein. Accordingly, the mimotopes of the present invention may consist of addition of N and/or C terminal extensions of a number of other natural residues at one or both ends. The peptide mimotopes may also be retro sequences of the natural sequences, in that the sequence orientation is reversed; or alternatively the sequences may be entirely or at least in part comprised of D-stereo isomer amino acids (inverso sequences). Also, the peptide sequences may be retro-inverso in character, in that the sequence orientation is reversed and the amino acids are of the D-stereoisomer form. Such retro or retro-inverso peptides have the advantage of being non-self, and as such may overcome problems of self-tolerance in the immune system.

Alternatively, peptide mimotopes may be identified using antibodies which are capable themselves of binding to the epitopes of the present invention using techniques such as phage display technology (EP 0 552 267 B1). This technique, generates a large number of peptide sequences which mimic the structure of the native peptides and are, therefore, capable of binding to anti-native peptide antibodies, but may not necessarily themselves share significant sequence homology to the native peptide. This approach may have significant advantages by allowing the possibility of identifying a peptide with enhanced immunogenic properties, or may overcome any potential self-antigen tolerance problems which may be associated with the use of the native peptide sequence. Additionally this technique allows the identification of a recognition pattern for each native-peptide in terms of its shared chemical properties amongst recognised mimotope sequences.

The covalent coupling of the peptide to the immunogenic carrier can be carried out in a manner well known in the art. Thus, for example, for direct covalent coupling it is possible to utilise a carbodiimide, glutaraldehyde or (N-[γ-maleimidobutyryloxy]succinimide ester, utilising common commercially available heterobifunctional linkers such as CDAP and SPDP (using manufacturers instructions). After the coupling reaction, the immunogen can easily be isolated and purified by means of a dialysis method, a gel filtration method, a fractionation method etc.

The types of carriers used in the immunogens of the present invention will be readily known to the man skilled in the art. The function of the carrier is to provide cytokine help in order to help induce an immune response against the peptide. A non-exhaustive list of carriers which may be used in the present invention include: Keyhole limpet Haemocyanin (KLH), serum albumins such as bovine serum albumin (BSA), inactivated bacterial toxins such as tetanus or diptheria toxins (TT and DT), or recombinant fragments thereof (for example, Domain 1 of Fragment C of TT, or the translocation domain of DT), or the purified protein derivative of tuberculin (PPD). Alternatively the mimotopes or epitopes may be directly conjugated to liposome carriers, which may additionally comprise immunogens capable of providing T-cell help. Preferably the ratio of mimotopes to carrier is in the order of 1:1 to 20:1, and preferably each carrier should carry between 3-15 peptides.

In an embodiment of the invention a preferred carrier is Protein D from *Haemophilus influenzae* (EP 0 594 610 B1). Protein D is an IgD-binding protein from *Haemophilus influenzae* and has been patented by Forsgren (WO 91/18926, granted EP 0 594 610 B1). In some circumstances, for example in recombinant immunogen expression systems it may be desirable to use fragments of protein D, for example Protein D $^{1/3rd}$ (comprising the N-terminal 100-110 amino acids of protein D (GB 9717953.5)).

Another preferred method of presenting the peptides of the present invention is in the context of a recombinant fusion molecule. For example, EP 0 421 635 B describes the use of chimaeric hepadnavirus core antigen particles to present foreign peptide sequences in a virus-like particle. As such, immunogens of the present invention may comprise peptides presented in chimaeric particles consisting of hepatitis B core antigen. Additionally, the recombinant fusion proteins may comprise the mimotopes of the present invention and a carrier protein, such as NS1 of the influenza virus. For any recombinantly expressed protein which forms part of the present invention, the nucleic acid which encodes said immunogen also forms an aspect of the present invention.

Peptides used in the present invention can be readily synthesised by solid phase procedures well known in the art. Suitable syntheses may be performed by utilising "T-boc" or "F-moc" procedures. Cyclic peptides can be synthesised by the solid phase procedure employing the well-known "F-moc" procedure and polyamide resin in the fully automated apparatus. Alternatively, those skilled in the art will know the necessary laboratory procedures to perform the process manually. Techniques and procedures for solid phase synthesis are described in 'Solid Phase Peptide Synthesis: A Practical Approach' by E. Atherton and R. C. Sheppard, published by IRL at Oxford University Press (1989). Alternatively, the peptides may be produced by recombinant methods, including expressing nucleic acid molecules encoding the mimotopes in a bacterial or mammalian cell line, followed by purification of the expressed mimotope. Techniques for recombinant expression of peptides and proteins are known in the art, and are described in Maniatis, T., Fritsch, E. F. and Sambrook et al., *Molecular cloning, a laboratory manual*, 2nd Ed.; Cold Spring Harbor Laboratory Press, Cold Spring Harbor, N.Y. (1989).

In a further embodiment of the invention is provided a method of producing a polypeptide as described herein. The process of the invention may be performed by conventional recombinant techniques such as described in Maniatis et al., Molecular Cloning—A Laboratory Manual; Cold Spring Harbor, 1982-1989. Accordingly there is provided a process for producing a polypeptide according to the invention, comprising culturing a host cell under conditions sufficient for the production of said polypeptide and recovering the polypeptide from the culture medium. In particular, the process of the invention may preferably comprise the steps of:

i) preparing a replicable or integrating expression vector capable, in a host cell, of expressing a DNA polymer comprising a nucleotide sequence that encodes the protein or an immunogenic derivative thereof;

ii) transforming a host cell with said vector;

ii) culturing said transformed host cell under conditions permitting expression of said DNA polymer to produce said protein; and iv) recovering said protein.

The polypeptides or immunogenic fragment of the invention may be in the form of the "mature" protein or may be a part of a larger protein such as a precursor or a fusion protein. It is often advantageous to include an additional amino acid sequence which contains secretory or leader sequences, pro-sequences, sequences which aid in purification such as multiple histidine residues, or an additional sequence for stability during recombinant production. Furthermore, addition of exogenous polypeptide or lipid tail or polynucleotide sequences to increase the immunogenic potential of the final molecule is also considered.

In one aspect, the invention relates to genetically engineered soluble fusion proteins comprising a polypeptide of the present invention, or a fragment thereof, and various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In a particular embodiment, the Fc part can be removed simply by incorporation of a cleavage sequence which can be cleaved with blood clotting factor Xa. Furthermore, this invention relates to processes for the preparation of these fusion proteins by genetic engineering, and to the use thereof for drug screening, diagnosis and therapy. A particularly preferred aspect of the invention relates to the use of a polypeptide or a polynucleotide in the manufacture of a vaccine for immunotherapeutically treating a patient suffering from or susceptible to carcinoma, especially colon cancer or other colon-associated tumours or diseases. A further aspect of the invention also relates to polynucleotides encoding such fusion proteins. Examples of fusion protein technology can be found in International Patent Application Nos. WO94/29458 and WO94/22914.

The proteins may be chemically conjugated, or expressed as recombinant fusion proteins allowing increased levels to be produced in an expression system as compared to non-fused protein. The fusion partner may assist in providing T helper epitopes (immunological fusion partner), preferably T helper epitopes recognised by humans, or assist in expressing the protein (expression enhancer) at higher yields than the native recombinant protein. Preferably the fusion partner will be both an immunological fusion partner and expression enhancing partner.

Fusion partners include protein D from *Haemophilus influenza* B and the non-structural protein from influenzae virus, NS1 (hemagglutinin). Another immunological fusion partner is the protein known as LYTA. Preferably the C terminal portion of the molecule is used. Lyta is derived from *Streptococcus pneumoniae* which synthesize an N-acetyl-L-alanine amidase, amidase LYTA, (coded by the lytA gene {Gene, 43 (1986) page 265-272} an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at its amino terminus has been described {Biotechnology: 10, (1992) page 795-798}. It is possible to use the repeat portion of the Lyta molecule found in the C terminal end starting at residue 178, for example residues 188-305.

The present invention also includes xenogeneic forms (also termed ortholog forms) of the aforementioned polypeptides, said xenogeneic forms referring to an antigen having substantial sequence identity to the human antigen (also termed autologous antigen) which serves as a reference antigen but which is derived from a different non-human species. In this context the substantial identity refers to concordance of an amino acid sequence with another amino acid sequence or of a polynucleotide sequence with another polynucleotide sequence when such sequence are arranged in a best fit alignment in any of a number of sequence alignment proteins known in the art. By substantial identity is meant at least 70-95%, and preferably at least 85-95%, most preferably at least 90%-95%, sequence identity between the compared sequences. Therefore according to the invention the xenogeneic CASB7439 polypeptide will be a CASB7439 polypeptide which is xenogeneic with respect to human CASB7439, in other words which is isolated from a species other than human. In a preferred embodiment, the polypeptide is isolated from mouse, rat, pig, or rhesus monkey, most preferably from mouse or rat. Accordingly the present invention also provides a method of inducing an immune response against human CASB7439 having an amino acid sequence as set forth in any of the sequences SEQ ID NO:2, SEQ ID NO:3, SEQ ID NO:7, SEQ ID NO:10 or SEQ ID NO:11 in a human, comprising administering to the subject an effective dosage of a composition comprising a xenogeneic form of said human CASB7439 as described herein. A preferred embodiment is a method of inducing an immune response against human CASB7439 using the xenogeneic CASB7439 isolated from mouse, rat, pig or rhesus monkey. Another preferred method of inducing an immune response according to the present invention is using an antigen composition including a live viral expression system which expresses said xenogeneic antigen. The preferred xenogeneic CASB7439 polypeptide has the sequence set forth in SEQ ID NO:12 (mouse) or in SEQ ID NO:14 (rat).

The isolated xenogeneic CASB7439 polypeptide will generally share substantial sequence similarity, and include isolated polypeptides comprising an amino acid sequence which has at least 70% identity, preferably at least 80% identity, more preferably at least 90% identity, yet more preferably at least 95% identity, most preferably at least 97-99% identity, to that of SEQ ID NO:12 or SEQ ID NO:14 over the entire length of SEQ ID NO:12 or SEQ ID NO:14. Accordingly the xenogeneic polypeptide will comprise an immunogenic fragment of the polypeptide of SEQ ID NO:12 or SEQ ID NO:14 in which the immunogenic activity of the immunogenic fragment is substantially the same as the polypeptide of SEQ ID NO:12 or SEQ ID NO:14. In addition the xenogeneic CASB7439 polypeptide can be a fragment of at least about 20 consecutive amino acids, preferably about 30, more preferably about 50, yet more preferably about 100, most preferably about 150 contiguous amino acids selected from the amino acid sequences as shown in SEQ ID NO:12 or in SEQ ID NO:14. More particularly xenogeneic CASB7439 fragments will retain some functional property, preferably an immunological activity, of the larger molecule set forth in SEQ ID NO:12 or in SEQ ID NO14, and are useful in the methods described herein (e.g. in pharmaceutical and vaccine compositions, in diagnostics, etc.). In particular the fragments will be able to generate an immune response against the human counterpart, such as the generation of cross-reactive antibodies which react with the autologous human form of CASB7439 as set forth in any of the SEQ ID NO: 2. In a specific embodiment, the xenogeneic polypeptide of the invention may be part of a larger fusion, comprising the xenogeneic CASB7439 polypeptide or fragment thereof and a heterologous protein or part of a protein acting as a fusion partner as described hereabove.

The present invention also includes variants of the aforementioned polypeptides, that is polypeptides that vary from the referents by conservative amino acid substitutions, whereby a residue is substituted by another with like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5-10, 1-5, 1-3, 1-2 or 1 amino acids are substituted, deleted, or added in any combination.

Polypeptides of the present invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

In a further aspect, the present invention relates to CASB7439 polynucleotides. Such polynucleotides include isolated polynucleotides comprising a nucleotide sequence encoding a polypeptide which has at least 70% identity, preferably at least 80% identity, more preferably at least 90% identity, yet more preferably at least 95% identity, to the amino acid sequence of SEQ ID NO:2, SEQ ID NO:3, SEQ ID NO:7, SEQ ID NO:10 or SEQ ID NO:11, over the entire length of SEQ ID NO:2, SEQ ID NO:3, SEQ ID NO:7, SEQ ID NO:10 or SEQ ID NO:11 respectively. In this regard, encoded polypeptides which have at least 97% identity are highly preferred, whilst those with at least 98-99% identity are more highly preferred, and those with at least 99% identity are most highly preferred.

Further polynucleotides of the present invention include isolated polynucleotides comprising a nucleotide sequence that has at least 70% identity, preferably at least 80% identity, more preferably at least 90% identity, yet more preferably at least 95% identity, to a nucleotide sequence encoding a polypeptide of SEQ ID NO:2, SEQ ID NO:3, SEQ ID NO:7, SEQ ID NO:10, or SEQ ID NO:11, over the entire coding region. In this regard, polynucleotides which have at least 97% identity are highly preferred, whilst those with at least 98-99% identity are more highly preferred, and those with at least 99% identity are most highly preferred.

Further polynucleotides of the present invention include isolated polynucleotides comprising a nucleotide sequence which has at least 70% identity, preferably at least 80% identity, more preferably at least 90% identity, yet more preferably at least 95% identity, to SEQ ID NO:1, SEQ ID NO:4, SEQ ID NO:5, SEQ ID NO:6, SEQ ID NO:8 or SEQ ID NO:9, over the entire length of said sequences, or to the coding sequence of SEQ ID NO:1, SEQ ID NO:4, SEQ ID NO:5, SEQ ID NO:6, SEQ ID NO:8 or SEQ ID NO:9 over the entire length of said coding sequence of SEQ ID NO:1, SEQ ID NO:4, SEQ ID NO:5, SEQ ID NO:6, SEQ ID NO:8 or SEQ ID NO:9. In this regard, polynucleotides which have at least 97% identity are highly preferred, whilst those with at least 98-99% identity are more highly preferred, and those with at least 99% identity are most highly preferred. Such polynucleotides include a polynucleotide comprising the polynucleotide of SEQ ID NO:1, SEQ ID NO:4, SEQ ID NO:5, SEQ ID NO:6, SEQ ID NO:8 or SEQ ID NO:9 as well as the polynucleotide of SEQ ID NO:1, SEQ ID NO:4, SEQ ID NO:5, SEQ ID NO:6, SEQ ID NO:8, SEQ ID NO:9 or the coding region of SEQ ID NO:1, SEQ ID NO:4, SEQ ID NO:5, SEQ ID NO:6, SEQ ID NO:8 or SEQ ID NO:9.

The present invention also provides a nucleic acid encoding the aforementioned xenogeneic proteins of the present invention and their use in medicine. In a preferred embodiment, the xenogeneic CASB7439 polynucleotide for use in pharmaceutical compositions has the sequence set forth in SEQ ID NO:13 (mouse) or in SEQ ID NO:15 (rat). The isolated xenogeneic CASB7439 polynucleotides according to the invention may be single-stranded (coding or antisense) or double-stranded, and may be DNA (genomic, cDNA or synthetic) or RNA molecules. Additional coding or non-coding sequences may, but need not, be present within a polynucleotide of the present invention. In other related embodiments, the present invention provides polynucleotide variants having substantial identity to the sequences disclosed herein in SEQ ID NO:13 or in SEQ ID NO:15, for example those comprising at least 70% sequence identity, preferably at least 75%, 80%, 85%, 90%, 95%, 96%, 97%, 98%, or 99% or higher, sequence identity compared to a polynucleotide sequence of this invention using the methods described herein, (e.g., BLAST analysis using standard parameters). In a related embodiment, the isolated xenogeneic polynucleotide of the invention will comprise a nucleotide sequence encoding a polypeptide that has at least 90%, preferably 95% and above, identity to the amino acid sequence of SEQ ID NO:12 or of SEQ ID NO:14, over the entire length of SEQ ID NO:12 or of SEQ ID NO:14; or a nucleotide sequence complementary to said isolated polynucleotide.

The invention also provides polynucleotides which are complementary to all the above described polynucleotides.

Said polynucleotides can be inserted in a suitable plasmid, recombinant microorganism vector or a recombinant live microorganism and used for immunization (see for example Wolff et. al., Science 247:1465-1468 (1990); Corr et. al., J. Exp. Med. 184:1555-1560 (1996); Doe et. al., Proc. Natl. Acad. Sci. 93:8578-8583 (1996)). Accordingly there is provided in the present invention an expression vector or recombinant live microorganism comprising said polynucleotides as hereabove defined.

The invention also provides a fragment of a CASB7439 polynucleotide which when administered to a subject has the same immunogenic properties as the polynucleotide of SEQ ID NO:1, SEQ ID NO:4, SEQ ID NO:5, SEQ ID NO:6, SEQ ID NO:8, SEQ ID NO:9, SEQ ID NO:13 or SEQ ID NO:15.

The invention also provides a polynucleotide encoding an immunological fragment of a CASB7439 polypeptide as hereinbefore defined.

The fragments have a level of immunogenic activity of at least about 50%, preferably at least about 70% and more preferably at least about 90% of the level of immunogenic activity of a polypeptide sequence set forth in SEQ ID NO:2, SEQ ID NO:3, SEQ ID NO:7, SEQ ID NO:10 or SEQ ID NO:11, SEQ ID NO:12 or SEQ ID NO:14 or a polypeptide sequence encoded by a polynucleotide sequence set forth in SEQ ID NO:1, SEQ ID NO:4, SEQ ID NO:5, SEQ ID NO:6, SEQ ID NO:8, SEQ ID NO:9, SEQ ID NO:13 or SEQ ID NO:15.

The polypeptide fragments according to the invention preferably comprise at least about 5, 10, 15, 20, 25, 50, or 100 contiguous amino acids, or more, including all intermediate lengths, of a polypeptide composition set forth herein, such as those set forth in SEQ ID NO:2, SEQ ID NO:3, SEQ ID NO:7, SEQ ID NO:10, SEQ ID NO:11, SEQ ID NO:12 or SEQ ID NO:14, or those encoded by a polynucleotide sequence set forth in a sequence of SEQ ID NO:1, SEQ ID NO:4, SEQ ID NO:5, SEQ ID NO:6, SEQ ID NO:8, SEQ ID NO:9, SEQ ID NO:13 or SEQ ID NO:15.

The nucleotide sequence of SEQ ID NO:1 is a cDNA sequence which comprises a polypeptide encoding sequence (nucleotide 545 to 1126) encoding a polypeptide of 193 amino acids, the polypeptide of SEQ ID NO:2. The nucleotide sequence encoding the polypeptide of SEQ ID NO:2 may be identical to the polypeptide encoding sequence contained in SEQ ID NO:1 or it may be a sequence other than the one contained in SEQ ID NO:1, which, as a result of the redundancy (degeneracy) of the genetic code, also encodes the polypeptide of SEQ ID NO:2. The polypeptide of the SEQ ID NO:2 is structurally related to other proteins of the achaete scute family, and is also named "human Achaete Scute homologue 2" (HASH2) (accession number NP_005161 and AAB86993).

Human Achaete Scute homologue 2 (HASH2) gene, officially designated human ASCL2 (Achaete Scute complex like 2) is a homologue of the *Drosophila* Achaete and Scute genes. Human ASCL2 is expressed in the extravillus trophoblasts of the developing placenta only, and maps on chromosome 11p15 close to IGF2 and H19. The mouse achaete-scute homolog-2 gene (MASH2) encodes a transcription factor playing a role in the development of the trophoblast. The Mash2 gene is paternally imprinted in the mouse, and the lack of human ASCL2 expression in non-malignant hydatidiform (androgenetic) moles indicates that human Ascl2 is also imprinted in man.

Ascl2 genes are members of the basic helix-loop-helix (BHLH) family of transcription factors. They activate transcription by binding to the E box (5'-CANNTG-3'). Dimerization with other BHLH proteins is required for efficient DNA binding. They are involved in the determination of the neuronal precursors in the peripheral nervous system and the central nervous system in *drosophila melanogaster*, and probably in mammals as well.

The complementary strand of the nucleotide sequence of SEQ ID NO:1 is the polynucleotide sequence of SEQ ID NO:6. This strand also comprises two other polypeptide encoding sequences. The first polypeptide encoding sequence (nucleotide 1184 to 399 of SEQ ID:1, nucleotide 608 to 1393 of SEQ ID NO:6) encodes a polypeptide of 262 amino acids, the polypeptide of SEQ ID NO:3. The second polypeptide encoding sequence (nucleotide 840 to 262 of SEQ ID NO:1, nucleotide 952 to 1530 of SEQ ID NO:6) encodes a polypeptide of 193 amino acids, the polypeptide of SEQ ID NO: 11. The nucleotide sequence encoding the polypeptides of SEQ ID NO:3 and SEQ ID NO:11 may be identical to the polypeptides encoding sequence contained in SEQ ID NO: 6 or it may be a sequence other than the one contained in SEQ ID NO: 6, which, as a result of the redundancy (degeneracy) of the genetic code, also encodes the polypeptides of SEQ ID NO:3 and 11. The polypeptide of the SEQ ID NO:3 is structurally related to other proteins of the splicing coactivator protein family, having homology and/or structural similarity with *homo sapiens* splicing coactivator subunit srm300 (genbank accession AAF21439). The polypeptide of SEQ ID NO:11 is not related to any known protein. Polypeptide sequences as set forth in SEQ ID NO:3 and SEQ ID NO:11, and polynucleotide sequences as set forth in SEQ ID NO:6 are novel and also form part of the invention.

Preferred polypeptides and polynucleotides of the present invention are expected to have, inter alia, similar biological functions/properties to their homologous polypeptides and polynucleotides. Furthermore, preferred polypeptides, immunological fragments and polynucleotides of the present invention have at least one activity of either SEQ ID NO:1, SEQ ID NO:2, SEQ ID NO:3 or SEQ ID NO:11 as appropriate.

The present invention also relates to partial or other incomplete polynucleotide and polypeptide sequences which were first identified prior to the determination of the corresponding full length sequences of SEQ ID NO:1, SEQ ID NO:2, SEQ ID NO:3, and SEQ ID NO:11.

Accordingly, in a further aspect, the present invention provides for an isolated polynucleotide which:
(a) comprises a nucleotide sequence which has at least 70% identity, preferably at least 80% identity, more preferably at least 90% identity, yet more preferably at least 95% identity, even more preferably at least 97-99% identity to SEQ ID NO:4 and 5 over the entire length of SEQ ID NO 4 and 5;
(b) has a nucleotide sequence which has at least 70% identity, preferably at least 80% identity, more preferably at least 90% identity, yet more preferably at least 95% identity, even more preferably at least 97-99% identity, to SEQ ID NO:1 or SEQ ID NO:6 over the entire length of SEQ ID NO:4 and SEQ ID NO:5 respectively;
(c) the polynucleotide of SEQ ID NO:4 and SEQ ID NO:5; or
(d) a nucleotide sequence encoding a polypeptide which has at least 70% identity, preferably at least 80% identity, more preferably at least 90% identity, yet more preferably at least 95% identity, even more preferably at least 97-99% identity, to the amino acid sequence of SEQ ID NO:2 and SEQ ID NO:7 respectively, over the entire length of SEQ ID NO:2 and 7, as well as the polynucleotides of SEQ ID NO:4 and 5.

The present invention further provides for a polypeptide which:
(a) comprises an amino acid sequence which has at least 70% identity, preferably at least 80% identity, more preferably at least 90% identity, yet more preferably at least 95% identity, most preferably at least 97-99% identity, to that of SEQ ID NO:2 and 7 over the entire length of SEQ ID NO:2 or 7;
(b) has an amino acid sequence which is at least 70% identity, preferably at least 80% identity, more preferably at least 90% identity, yet more preferably at least 95% identity, most preferably at least 97-99% identity, to the amino acid sequence of SEQ ID NO:2 or 7 over the entire length of SEQ ID NO:2 or 7;
(c) comprises the amino acid of SEQ ID NO:2 or 7; and
(d) is the polypeptide of SEQ ID NO: 7;
as well as polypeptides encoded by a polynucleotide comprising the sequence contained in SEQ ID NO:4 and 5.

Polynucleotides of the present invention may be obtained, using standard cloning and screening techniques, from a cDNA library derived from mRNA in cells of human colon cancer, (for example Sambrook et al., Molecular Cloning: A Laboratory Manual, 2$^{nd}$ Ed., Cold Spring harbor Laboratory Press, Cold Spring harbor, N.Y. (1989)). Polynucleotides of the invention can also be obtained from natural sources such as genomic DNA libraries or can be synthesized using well known and commercially available techniques.

When polynucleotides of the present invention are used for the recombinant production of polypeptides of the present invention, the polynucleotide may include the coding sequence for the mature polypeptide, by itself; or the coding sequence for the mature polypeptide in reading frame with other coding sequences, such as those encoding a leader or secretory sequence, a pre-, or pro- or prepro-protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., Proc Natl Acad Sci USA (1989) 86:821-824, or is an HA tag. The polynucleotide may also contain non-coding 5' and 3' sequences, such as transcribed, non-translated sequences, splicing and polyadenylation signals, ribosome binding sites and sequences that stabilize mRNA.

Further embodiments of the present invention include polynucleotides encoding polypeptide variants which comprise the amino acid sequence of SEQ ID NO:2, SEQ ID NO:3, SEQ ID NO:7, SEQ ID NO:11, SEQ ID NO:13 or SEQ ID NO:15 and in which several, for instance from 5 to 10, 1 to 5, 1 to 3, 1 to 2 or 1, amino acid residues are substituted, deleted or added, in any combination.

Polynucleotides which are identical or sufficiently identical to a nucleotide sequence contained in SEQ ID NO:1 or in SEQ ID NO:6, may be used as hybridization probes for cDNA and genomic DNA or as primers for a nucleic acid amplification (PCR) reaction, to isolate full-length cDNAs and genomic clones encoding polypeptides of the present invention and to isolate cDNA and genomic clones of other genes (including genes encoding paralogs from human sources and orthologs and paralogs from species other than human) that have a high sequence similarity to SEQ ID NO:1 or to SEQ ID NO:6. Typically these nucleotide sequences are 70% identical, preferably 80% identical, more preferably 90% identical, most preferably 95% identical to that of the referent. The probes or primers will generally comprise at least 15 nucleotides, preferably, at least 30 nucleotides and may have at least 50 nucleotides. Particularly preferred probes will have between 30 and 50 nucleotides. Particularly preferred primers will have between 20 and 25 nucleotides.

In particular, polypeptides or polynucleotides derived from sequences from homologous animal origin could be used as immunogens to obtain a cross-reactive immune response to the human gene.

A polynucleotide encoding a polypeptide of the present invention, including homologs from species other than human, may be obtained by a process which comprises the steps of screening an appropriate library under stringent hybridization conditions with a labeled probe having the sequence of SEQ ID NO: 1 or SEQ ID NO:6 or a fragment thereof; and isolating full-length cDNA and genomic clones containing said polynucleotide sequence. Such hybridization techniques are well known to the skilled artisan. Preferred stringent hybridization conditions include overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 microgram/ml denatured, sheared salmon sperm DNA; followed by washing the filters in 0.1×SSC at about 65° C. Thus the present invention also includes polynucleotides obtainable by screening an appropriate library under stingent hybridization conditions with a labeled probe having the sequence of SEQ ID NO:1 or SEQ ID NO:6 or a fragment thereof.

The skilled artisan will appreciate that, in many cases, an isolated cDNA sequence will be incomplete, in that the region coding for the polypeptide is short at the 5' end of the cDNA.

There are several methods available and well known to those skilled in the art to obtain full-length cDNAs, or extend short cDNAs, for example those based on the method of Rapid Amplification of cDNA ends (RACE) (see, for example, Frohman et al., PNAS USA 85, 8998-9002, 1988). Recent modifications of the technique, exemplified by the Marathon™ technology (Clontech Laboratories Inc.) for example, have significantly simplified the search for longer cDNAs. In the Marathon™ technology, cDNAs have been prepared from mRNA extracted from a chosen tissue and an 'adaptor' sequence ligated onto each end. Nucleic acid amplification (PCR) is then carried out to amplify the 'missing' 5' end of the cDNA using a combination of gene specific and adaptor specific oligonucleotide primers. The PCR reaction is then repeated using 'nested' primers, that is, primers designed to anneal within the amplified product (typically an adaptor specific primer that anneals further 3' in the adaptor sequence and a gene specific primer that anneals further 5' in the known gene sequence). The products of this reaction can then be analysed by DNA sequencing and a full-length cDNA constructed either by joining the product directly to the existing cDNA to give a complete sequence, or carrying out a separate full-length PCR using the new sequence information for the design of the 5' primer.

Recombinant polypeptides of the present invention may be prepared by processes well known in the art from genetically engineered host cells comprising expression systems. Accordingly, in a further aspect, the present invention relates to an expression system which comprises a polynucleotide of the present invention, to host cells which are genetically engineered with such expression sytems and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., Basic Methods in Molecular Biology (1986) and Sambrook et al., Molecular Cloning: A Laboratory Manual, 2nd Ed., Cold Spring Harbor Laboratory Press, Cold Spring Harbor, N.Y. (1989). Preferred such methods include, for instance, calcium phosphate transfection, DEAE-dextran mediated transfection, transvection, microinjection, cationic lipid-mediated transfection, electroporation, transduction, scrape loading, ballistic introduction or infection.

Preferably the proteins of the invention are coexpressed with thioredoxin in trans (TIT). Coexpression of thioredoxin in trans versus in cis is preferred to keep antigen free of thioredoxin without the need for protease. Thioredoxin coexpression eases the solubilisation of the proteins of the invention. Thioredoxin coexpression has also a significant impact on protein purification yield, on purified-protein solubility and quality.

Representative examples of appropriate hosts include bacterial cells, such as *Streptococci, Staphylococci, E. coli, Streptomyces* and *Bacillus subtilis* cells; fungal cells, such as yeast cells and *Aspergillus* cells; insect cells such as *Drosophila* S2 and *Spodoptera* Sf9 cells; animal cells such as CHO, COS, HeLa, C127, 3T3, BHK, HEK 293 and Bowes melanoma cells; and plant cells.

A great variety of expression systems can be used, for instance, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector which is able to maintain, propagate or express a polynucleotide to produce a polypeptide in a host may be used. The appropriate nucleotide sequence may be inserted into an expression system by any of a variety of well-known and routine techniques, such as, for example, those set forth in Sambrook et al., Molecular Cloning, A Laboratory Manual (supra). Appropriate secretion signals may be incorporated into the desired polypeptide to allow secretion of the translated protein into the lumen of the endoplasmic reticulum, the periplasmic space or the extracellular environment. These signals may be endogenous to the polypeptide or they may be heterologous signals.

The expression system may also be a recombinant live microorganism, such as a virus or bacterium. The gene of interest can be inserted into the genome of a live recombinant virus or bacterium. Inoculation and in vivo infection with this live vector will lead to in vivo expression of the antigen and induction of immune responses.

Therefore, in certain embodiments, polynucleotides encoding immunogenic polypeptides of the present invention are introduced into suitable mammalian host cells for expression using any of a number of known viral-based systems. In one illustrative embodiment, retroviruses provide a convenient and effective platform for gene delivery systems. A selected nucleotide sequence encoding a polypeptide of the present invention can be inserted into a vector and packaged in retroviral particles using techniques known in the art. The recombinant virus can then be isolated and delivered to a subject. A number of illustrative retroviral systems have been described (e.g., U.S. Pat. No. 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

In addition, a number of illustrative adenovirus-based systems have also been described. Unlike retroviruses which integrate into the host genome, adenoviruses persist extrachromosomally thus minimizing the risks associated with insertional mutagenesis (Haj-Ahmad and Graham (1986) J. Virol. 57:267-274; Bett et al. (1993) J. Virol. 67:5911-5921; Mittereder et al. (1994) Human Gene Therapy 5:717-729; Seth et al. (1994) J. Virol. 68:933-940; Barr et al. (1994) Gene Therapy 1:51-58; Berkner, K. L. (1988) BioTechniques 6:616-629; and Rich et al. (1993) Human Gene Therapy 4:461-476).

Various adeno-associated virus (AAV) vector systems have also been developed for polynucleotide delivery. AAV vectors can be readily constructed using techniques well known in the art. See, e.g., U.S. Pat. Nos. 5,173,414 and 5,139,941; International Publication Nos. WO 92/01070 and WO 93/03769; Lebkowski et al. (1988) Molec. Cell. Biol. 8:3988-3996; Vincent et al. (1990) Vaccines 90 (Cold Spring Harbor Laboratory Press); Carter, B. J. (1992) Current Opinion in Biotechnology 3:533-539; Muzyczka, N. (1992) Current Topics in Microbiol. and Immunol. 158:97-129; Kotin, R. M. (1994) Human Gene Therapy 5:793-801; Shelling and Smith (1994) Gene Therapy 1:165-169; and Zhou et al. (1994) J. Exp. Med. 179:1867-1875.

Additional viral vectors useful for delivering the nucleic acid molecules encoding polypeptides of the present invention by gene transfer include those derived from the pox family of viruses, such as vaccinia virus and avian poxvirus. By way of example, vaccinia virus recombinants expressing the novel molecules can be constructed as follows. The DNA encoding a polypeptide is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the polypeptide of interest into the viral genome. The resulting TK.sup.(−) recombinant can be selected by culturing the cells in the presence of 5-bromodeoxyuridine and picking viral plaques resistant thereto.

A vaccinia-based infection/transfection system can be conveniently used to provide for inducible, transient expression or coexpression of one or more polypeptides described herein in host cells of an organism. In this particular system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide or polynucleotides of interest, driven by a T7 promoter. The polymerase expressed in the cytoplasm from the vaccinia virus recombinant transcribes the transfected DNA into RNA which is then translated into polypeptide by the host translational machinery. The method provides for high level, transient, cytoplasmic production of large quantities of RNA and its translation products. See, e.g., Elroy-Stein and Moss, Proc. Natl. Acad. Sci. USA (1990) 87:6743-6747; Fuerst et al. Proc. Natl. Acad. Sci. USA (1986) 83:8122-8126.

Alternatively, avipoxviruses, such as the fowlpox and canarypox viruses, can also be used to deliver the coding sequences of interest. Recombinant avipox viruses, expressing immunogens from mammalian pathogens, are known to confer protective immunity when administered to non-avian species. The use of an Avipox vector is particularly desirable in human and other mammalian species since members of the Avipox genus can only productively replicate in susceptible avian species and therefore are not infective in mammalian cells. Methods for producing recombinant Avipoxviruses are known in the art and employ genetic recombination, as described above with respect to the production of vaccinia viruses. See, e.g., WO 91/12882; WO 89/03429; and WO 92/03545.

Any of a number of alphavirus vectors can also be used for delivery of polynucleotide compositions of the present invention, such as those vectors described in U.S. Pat. Nos. 5,843, 723; 6,015,686; 6,008,035 and 6,015,694. Certain vectors based on Venezuelan Equine Encephalitis (VEE) can also be used, illustrative examples of which can be found in U.S. Pat. Nos. 5,505,947 and 5,643,576.

Moreover, molecular conjugate vectors, such as the adenovirus chimeric vectors described in Michael et al. J. Biol. Chem. (1993) 268:6866-6869 and Wagner et al. Proc. Natl. Acad. Sci. USA (1992) 89:6099-6103, can also be used for gene delivery under the invention.

Additional illustrative information on these and other known viral-based delivery systems can be found, for example, in Fisher-Hoch et al., Proc. Natl. Acad. Sci. USA 86:317-321, 1989; Flexner et al., Ann. N.Y. Acad. Sci. 569: 86-103, 1989; Flexner et al., Vaccine 8:17-21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, Biotechniques 6:616-627, 1988; Rosenfeld et al., Science 252:431-434, 1991; Kolls et al., Proc. Natl. Acad. Sci. USA 91:215-219, 1994; Kass-Eisler et al., Proc. Natl. Acad. Sci. USA 90:11498-11502, 1993; Guzman et al., Circulation 88:2838-2848, 1993; and Guzman et al., Cir. Res. 73:1202-1207, 1993.

The recombinant live microorganisms described above can be virulent, or attenuated in various ways in order to obtain live vaccines. Such live vaccines also form part of the invention.

In certain embodiments, a polynucleotide may be integrated into the genome of a target cell. This integration may be in the specific location and orientation via homologous recombination (gene replacement) or it may be integrated in a random, non-specific location (gene augmentation). In yet further embodiments, the polynucleotide may be stably maintained in the cell as a separate, episomal segment of DNA. Such polynucleotide segments or "episomes" encode sequences sufficient to permit maintenance and replication independent of or in synchronization with the host cell cycle. The manner in which the expression construct is delivered to a cell and where in the cell the polynucleotide remains is dependent on the type of expression construct employed.

In another embodiment of the invention, a polynucleotide is administered/delivered as "naked" DNA, for example as described in Ulmer et al., Science 259:1745-1749, 1993 and reviewed by Cohen, Science 259:1691-1692, 1993. The uptake of naked DNA may be increased by coating the DNA onto biodegradable beads, which are efficiently transported into the cells.

In still another embodiment, a composition of the present invention can be delivered via a particle bombardment approach, many of which have been described. In one illustrative example, gas-driven particle acceleration can be achieved with devices such as those manufactured by Powderject Pharmaceuticals PLC (Oxford, UK) and Powderject Vaccines Inc. (Madison, Wis.), some examples of which are described in U.S. Pat. Nos. 5,846,796; 6,010,478; 5,865,796; 5,584,807; and EP Patent No. 0500 799. This approach offers a needle-free delivery approach wherein a dry powder formulation of microscopic particles, such as polynucleotide or polypeptide particles, are accelerated to high speed within a helium gas jet generated by a hand held device, propelling the particles into a target tissue of interest.

In a related embodiment, other devices and methods that may be useful for gas-driven needle-less injection of compositions of the present invention include those provided by Bioject, Inc. (Portland, Oreg.), some examples of which are described in U.S. Pat. Nos. 4,790,824; 5,064,413; 5,312,335; 5,383,851; 5,399,163; 5,520,639 and 5,993,412.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, ion metal affinity chromatography (IMAC) is employed for purification. Well known techniques for refolding proteins may be employed to regenerate active conformation when the polypeptide is denatured during intracellular synthesis, isolation and or purification.

Another important aspect of the invention relates to a method for inducing, re-inforcing or modulating an immunological response in a mammal which comprises inoculating the mammal with a fragment or the entire polypeptide or polynucleotide of the invention, adequate to produce antibody and/or T cell immune response for immunoprophylaxis or for therapeutic treatment of cancer, more particularly colorectal cancer, and autoimmune disease and related conditions. Yet another aspect of the invention relates to a method of inducing, re-inforcing or modulating immunological response in a mammal which comprises, delivering a polypeptide of the present invention via a vector or cell directing expression of the polynucleotide and coding for the polypeptide in vivo in order to induce such an immunological response to produce immune responses for prophylaxis or treatment of said mammal from diseases.

A further aspect of the invention relates to an immunological/vaccine formulation (composition) and to their use in medicine. These compositions, when introduced into a mammalian host, induce, re-inforce or modulate an immunological response in that mammal to a polypeptide of the present invention wherein the composition comprises a polypeptide or polynucleotide of the invention or an immunological fragment thereof as herein before defined. More particularly the immunogenic composition according to the present invention comprises a safe and effective amount of a CASB7439 polypeptide, or immunogenic fragment thereof wherein the CASB7439 polypeptide is selected from the group comprising SEQ ID NO:2, SEQ ID NO:3, SEQ ID NO:7, SEQ ID NO:10, SEQ ID NO:11, SEQ ID NO:12 or SEQ ID NO:14. In another embodiment, the immunogenic composition comprises a safe and effective amount of a CASB7439-encoding polynucleotide, or fragment thereof wherein the CASB7439-encoding polynucleotide is selected from the group comprising SEQ ID NO:1, SEQ ID NO:4, SEQ ID NO:5, SEQ ID NO:6, SEQ ID NO:8, SEQ ID NO:9, SEQ ID NO:13 or SEQ ID NO:15.

The vaccine formulation according to the invention may further comprise a suitable, i.e. pharmaceutically acceptable carrier. Since a polypeptide may be broken down in the stomach, it is preferably administered parenterally (for instance, subcutaneous, intramuscular, intravenous, or intradermal injection). Formulations suitable for parenteral administration include aqueous and non-aqueous sterile injection solutions which may contain anti-oxidants, buffers, bacteriostats and solutes which render the formulation isotonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use.

A further aspect of the invention relates to the in vitro induction of immune responses to a fragment or the entire polypeptide or polynucleotide of the present invention or a molecule comprising the polypeptide or polynucleotide of the present invention, using cells from the immune system of a mammal, and reinfusing these activated immune cells of the mammal for the treatment of disease. Activation of the cells from the immune system is achieved by in vitro incubation with the entire polypeptide or polynucleotide of the present invention or a molecule comprising the polypeptide or polynucleotide of the present invention in the presence or absence of various immunomodulator molecules. A further aspect of the invention relates to the immunization of a mammal by administration of antigen presenting cells modified by in vitro loading with part or the entire polypeptide of the present invention or a molecule comprising the polypeptide of the present invention and administered in vivo in an immunogenic way. Alternatively, antigen presenting cells can be transfected in vitro with a vector containing a fragment or the entire polynucleotide of the present invention or a molecule comprising the polynucleotide of the present invention, such as to express the corresponding polypeptide, and administered in vivo in an immunogenic way. Accordingly, the pharmaceutical compositions of the invention will comprise an effective amount of antigen presenting cells, modified by in vitro loading with a CASB7439 polypeptide, or genetically modified in vitro to express a CASB7439 polypeptide and a pharmaceutically effective carrier.

According to another embodiment, the pharmaceutical/immunogenic compositions described herein will comprise one or more immunostimulants in addition to the immunogenic polynucleotide, polypeptide, antibody, T-cell and/or antigen presenting cell (APC) compositions of this invention. Accordingly there is herein provided a process for the production of said immunogenic composition, comprising admixing a CASB7439 polypeptide or a CASB7439-encoding polynucleotide with a suitable adjuvant/immunostimulant, diluent or other pharmaceutically acceptable carrier. An immunostimulant refers to essentially any substance that enhances or potentiates an immune response (antibody and/or cell-mediated) to an exogenous antigen. One preferred type of immunostimulant comprises an adjuvant. Many adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Certain adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF, interleukin-2, -7, -12, and other like growth factors, may also be used as adjuvants.

Within certain embodiments of the invention, the adjuvant composition is preferably one that induces an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, *Ann. Rev. Immunol.* 7:145-173, 1989.

Certain preferred adjuvants for eliciting a predominantly Th1-type response include, for example, a combination of monophosphoryl lipid A, preferably 3-de-O-acylated monophosphoryl lipid A, together with an aluminum salt. MPL® adjuvants are available from Corixa Corporation (Seattle, Wash.; see, for example, U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462 Immunostimulatory DNA sequences are also described, for example, by Sato et al., Science 273:352, 1996. Another preferred adjuvant comprises a saponin, such as Quil A, or derivatives thereof, including QS21 and QS7 (Aquila Biopharmaceuticals Inc., Framingham, Mass.); Escin; Digitonin; or *Gypsophila* or *Chenopodium quinoa* saponins. Other preferred formulations include more than one saponin in the adjuvant combinations of the present invention, for example combinations of at least two of the following group comprising QS21, QS7, Quil A, β-escin, or digitonin.

Alternatively the saponin formulations may be combined with vaccine vehicles composed of chitosan or other polycationic polymers, polylactide and polylactide-co-glycolide particles, poly-N-acetyl glucosamine-based polymer matrix, particles composed of polysaccharides or chemically modified polysaccharides, liposomes and lipid-based particles, particles composed of glycerol monoesters, etc. The saponins may also be formulated in the presence of cholesterol to form particulate structures such as liposomes or ISCOMs. Furthermore, the saponins may be formulated together with a polyoxyethylene ether or ester, in either a non-particulate solution or suspension, or in a particulate structure such as a paucilamelar liposome or ISCOM. The saponins may also be formulated with excipients such as Carbopol® to increase viscosity, or may be formulated in a dry powder form with a powder excipient such as lactose.

In one preferred embodiment, the adjuvant system includes the combination of a monophosphoryl lipid A and a saponin derivative, such as the combination of QS21 and 3D-MPL® adjuvant, as described in WO 94/00153, or a less reactogenic composition where the QS21 is quenched with cholesterol, as described in WO 96/33739. Other preferred formulations comprise an oil-in-water emulsion and tocopherol. Another particularly preferred adjuvant formulation employing QS21, 3D-MPL® adjuvant and tocopherol in an oil-in-water emulsion is described in WO 95/17210.

Another enhanced adjuvant system involves the combination of a CpG-containing oligonucleotide and a saponin derivative particularly the combination of CpG and QS21 as disclosed in WO 00/09159. Preferably the formulation additionally comprises an oil in water emulsion and tocopherol.

Additional illustrative adjuvants for use in the pharmaceutical compositions of the invention include Montanide ISA 720 (Seppic, France), SAF (Chiron, Calif., United States), ISCOMS (CSL), MF-59 (Chiron), the SBAS series of adjuvants (e.g., SBAS-2 or SBAS-4, available from SmithKline Beecham, Rixensart, Belgium), Detox (Enhanzyn®) (Corixa, Hamilton, Mont.), RC-529 (Corixa, Hamilton, Mont.) and other aminoalkyl glucosaminide 4-phosphates (AGPs), such as those described in pending U.S. patent application Ser. Nos. 08/853,826 and 09/074,720, the disclosures of which are incorporated herein by reference in their entireties, and polyoxyethylene ether adjuvants such as those described in WO 99/52549A1.

Other preferred adjuvants include adjuvant molecules of the general formula (I):

Wherein, n is 1-50, A is a bond or —C(O)—, R is $C_{1-50}$ alkyl or Phenyl $C_{1-50}$ alkyl.

One embodiment of the present invention consists of a vaccine formulation comprising a polyoxyethylene ether of general formula (I), wherein n is between 1 and 50, preferably 4-24, most preferably 9; the R component is $C_{1-50}$, preferably $C_4$-$C_{20}$ alkyl and most preferably $C_{1-2}$ alkyl, and A is a bond. The concentration of the polyoxyethylene ethers should be in the range 0.1-20%, preferably from 0.1-10%, and most preferably in the range 0.1-1%. Preferred polyoxyethylene ethers are selected from the following group: polyoxyethylene-9-lauryl ether, polyoxyethylene-9-steoryl ether, polyoxyethylene-8-steoryl ether, polyoxyethylene-4-lauryl ether, polyoxyethylene-35-lauryl ether, and polyoxyethylene-23-lauryl ether. Polyoxyethylene ethers such as polyoxyethylene lauryl ether are described in the Merck index ($12^{th}$ edition: entry 7717). These adjuvant molecules are described in WO 99/52549.

The polyoxyethylene ether according to the general formula (I) above may, if desired, be combined with another adjuvant. For example, a preferred adjuvant combination is preferably with CpG as described in the pending UK patent application GB 9820956.2.

Preferably a carrier is also present in the vaccine composition according to the invention. The carrier may be an oil in water emulsion, or an aluminium salt, such as aluminium phosphate or aluminium hydroxide.

A preferred oil-in-water emulsion comprises a metabolisible oil, such as squalene, alpha tocopherol and Tween 80. In a particularly preferred aspect the antigens in the vaccine composition according to the invention are combined with QS21 and 3D-MPL in such an emulsion. Additionally the oil in water emulsion may contain span 85 and/or lecithin and/or tricaprylin.

Typically for human administration QS21 and 3D-MPL will be present in a vaccine in the range of 1 μg-200 μg, such as 10-100 μg, preferably 10 μg-50 μg per dose. Typically the oil in water will comprise from 2 to 10% squalene, from 2 to 10% alpha tocopherol and from 0.3 to 3% tween 80. Preferably the ratio of squalene:alpha tocopherol is equal to or less than 1 as this provides a more stable emulsion. Span 85 may also be present at a level of 1%. In some cases it may be advantageous that the vaccines of the present invention will further contain a stabiliser.

Non-toxic oil in water emulsions preferably contain a non-toxic oil, e.g. squalane or squalene, an emulsifier, e.g. Tween 80, in an aqueous carrier. The aqueous carrier may be, for example, phosphate buffered saline.

A particularly potent adjuvant formulation involving QS21, 3D-MPL and tocopherol in an oil in water emulsion is described in WO 95/17210.

The present invention also provides a polyvalent vaccine composition comprising a vaccine formulation of the invention in combination with other antigens, in particular antigens useful for treating cancers, more particularly colorectal cancer, autoimmune diseases and related conditions. Such a polyvalent vaccine composition may include a TH-1 inducing adjuvant as hereinbefore described.

According to another embodiment of this invention, an immunogenic composition described herein is delivered to a host via antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, Nature 392:245-251, 1998) and have been shown to be effective as a physiological adjuvant for eliciting prophylactic or therapeutic antitumor immunity (see Timmerman and Levy, Ann. Rev. Med. 50:507-529, 1999). In general, dendritic cells may be identified based on their typical shape (stellate in situ, with marked cytoplasmic processes (dendrites) visible in vitro), their ability to take up, process and present antigens with high efficiency and their ability to activate naïve T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., Nature Med. 4:594-600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs may generally be transfected with a polynucleotide of the invention (or portion or other variant thereof) such that the encoded polypeptide, or an immunogenic portion thereof, is expressed on the cell surface. Such transfection may take place ex vivo, and a pharmaceutical composition comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., Immunology and cell Biology 75:456-460, 1997. Antigen loading of dendritic cells may be achieved by incubating dendritic cells or progenitor cells with the tumor polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

While any suitable carrier known to those of ordinary skill in the art may be employed in the pharmaceutical compositions of this invention, the type of carrier will typically vary depending on the mode of administration. Compositions of the present invention may be formulated for any appropriate manner of administration, including for example, topical, oral, nasal, mucosal, intravenous, intracranial, intraperitoneal, subcutaneous and intramuscular administration.

Carriers for use within such pharmaceutical compositions are biocompatible, and may also be biodegradable. In certain embodiments, the formulation preferably provides a relatively constant level of active component release. In other embodiments, however, a more rapid rate of release immediately upon administration may be desired. The formulation of such compositions is well within the level of ordinary skill in the art using known techniques. Illustrative carriers useful in this regard include microparticles of poly(lactide-co-glycolide), polyacrylate, latex, starch, cellulose, dextran and the like. Other illustrative delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

In another illustrative embodiment, biodegradable microspheres (e.g., polylactate polyglycolate) are employed as carriers for the compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344, 5,407,609 and 5,942,252. Modified hepatitis B core protein carrier systems. such as described in WO/99 40934, and references cited therein, will also be useful for many applications. Another illustrative carrier/delivery system employs a carrier comprising particulate-protein complexes, such as those described in U.S. Pat. No. 5,928,647, which are capable of inducing a class I-restricted cytotoxic T lymphocyte responses in a host.

The pharmaceutical compositions of the invention will often further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

The pharmaceutical compositions described herein may be presented in unit-dose or multi-dose containers, such as sealed ampoules or vials. Such containers are typically sealed in such a way to preserve the sterility and stability of the formulation until use. In general, formulations may be stored as suspensions, solutions or emulsions in oily or aqueous vehicles. Alternatively, a pharmaceutical composition may be stored in a freeze-dried condition requiring only the addition of a sterile liquid carrier immediately prior to use.

The development of suitable dosing and treatment regimens for using the particular compositions described herein in a variety of treatment regimens, including e.g., oral, parenteral, intravenous, intranasal, and intramuscular administration and formulation, is well known in the art, some of which are briefly discussed below for general purposes of illustration.

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (see, for example, Mathiowitz et al., Nature 1997 Mar. 27; 386(6623):410-4; Hwang et al., Crit Rev Ther Drug Carrier Syst 1998; 15(3):243-84; U.S. Pat. No. 5,641,515; U.S. Pat. No. 5,580,579 and U.S. Pat. No. 5,792,451). Tablets, troches, pills, capsules and the like may also contain any of a variety of additional components, for example, a binder, such as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. Of course, any material used in preparing any dosage unit form should be pharmaceutically pure and substantially non-toxic in the amounts employed. In addition, the active compounds may be incorporated into sustained-release preparation and formulations.

Typically, these formulations will contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally-administered formulation. Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

In certain circumstances it will be desirable to deliver the pharmaceutical compositions disclosed herein parenterally, intravenously, intramuscularly, or even intraperitoneally. Such approaches are well known to the skilled artisan, some of which are further described, for example, in U.S. Pat. No. 5,543,158; U.S. Pat. No. 5,641,515 and U.S. Pat. No. 5,399,363. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations generally will contain a preservative to prevent the growth of microorganisms.

Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. Moreover, for human administration, preparations will of course preferably meet sterility, pyrogenicity, and the general safety and purity standards as required by FDA Office of Biologics standards.

In another embodiment of the invention, the compositions disclosed herein may be formulated in a neutral or salt form. Illustrative pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human.

In certain embodiments, the pharmaceutical compositions may be delivered by intranasal sprays, inhalation, and/or other aerosol delivery vehicles. Methods for delivering genes, nucleic acids, and peptide compositions directly to the lungs via nasal aerosol sprays has been described, e.g., in U.S. Pat. No. 5,756,353 and U.S. Pat. No. 5,804,212. Likewise, the delivery of drugs using intranasal microparticle resins (Takenaga et al., J Controlled Release 1998 Mar. 2; 52(1-2):81-7) and lysophosphatidyl-glycerol compounds (U.S. Pat. No. 5,725,871) are also well-known in the pharmaceutical arts. Likewise, illustrative transmucosal drug delivery in the form of a polytetrafluoroetheylene support matrix is described in U.S. Pat. No. 5,780,045.

In certain embodiments, liposomes, nanocapsules, microparticles, lipid particles, vesicles, and the like, are used for the introduction of the compositions of the present invention into suitable host cells/organisms. In particular, the compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles.

The formation and use of liposome and liposome-like preparations as potential drug carriers is generally known to those of skill in the art (see for example, Lasic, Trends Biotechnol 1998 July; 16(7):307-21; Takakura, Nippon Rinsho 1998 March; 56(3):691-5; Chandran et al., Indian J Exp Biol. 1997 August; 35(8):801-9; Margalit, Crit Rev Ther Drug Carrier Syst. 1995; 12(2-3):233-61; U.S. Pat. No. 5,567,434; U.S. Pat. No. 5,552,157; U.S. Pat. No. 5,565,213; U.S. Pat. No. 5,738,868 and U.S. Pat. No. 5,795,587, each specifically incorporated herein by reference in its entirety).

Liposomes have been used successfully with a number of cell types that are normally difficult to transfect by other procedures, including T cell suspensions, primary hepatocyte cultures and PC 12 cells (Renneisen et al., J Biol Chem. 1990 Sep. 25; 265(27):16337-42; Muller et al., DNA Cell Biol. 1990 April; 9(3):221-9). In addition, liposomes are free of the DNA length constraints that are typical of viral-based delivery systems. Liposomes have been used effectively to introduce genes, various drugs, radiotherapeutic agents, enzymes, viruses, transcription factors, allosteric effectors and the like, into a variety of cultured cell lines and animals. Furthermore, he use of liposomes does not appear to be associated with autoimmune responses or unacceptable toxicity after systemic delivery.

In certain embodiments, liposomes are formed from phospholipids that are dispersed in an aqueous medium and spontaneously form multilamellar concentric bilayer vesicles (also termed multilamellar vesicles (MLVs).

Alternatively, in other embodiments, the invention provides for pharmaceutically-acceptable nanocapsule formulations of the compositions of the present invention. Nanocapsules can generally entrap compounds in a stable and reproducible way (see, for example, Quintanar-Guerrero et al., Drug Dev Ind Pharm. 1998 December; 24(12):1113-28). To avoid side effects due to intracellular polymeric overloading, such ultrafine particles (sized around 0.1 µm) may be designed using polymers able to be degraded in vivo. Such particles can be made as described, for example, by Couvreur et al., Crit Rev Ther Drug Carrier Syst. 1988; 5(1):1-20; zur Muhlen et al., Eur J Pharm Biopharm. 1998 March; 45(2): 149-55; Zambaux et al. J Controlled Release. 1998 Jan. 2; 50(1-3):31-40; and U.S. Pat. No. 5,145,684.

This invention also relates to the use of polynucleotides, in the form of primers derived from the polynucleotides of the present invention, and of polypeptides, in the form of antibodies or reagents specific for the polypeptide of the present invention, as diagnostic reagents.

The identification of genetic or biochemical markers in blood or tissues that will enable the detection of very early changes along the carcinogenesis pathway will help in determining the best treatment for the patient. Surrogate tumour markers, such as polynucleotide expression, can be used to diagnose different forms and states of cancer. The identification of expression levels of the polynucleotides of the invention will be useful in both the staging of the cancerous disorder and grading the nature of the cancerous tissue. The staging process monitors the advancement of the cancer and is determined on the presence or absence of malignant tissue in the areas biopsied. The polynucleotides of the invention can help to perfect the staging process by identifying markers for the aggresivity of a cancer, for example the presence in different areas of the body. The grading of the cancer describes how closely a tumour resembles normal tissue of its same type and is assessed by its cell morphology and other markers of differentiation. The polynucleotides of the invention can be useful in determining the tumour grade as they can help in the determination of the differentiation status of the cells of a tumour.

The diagnostic assays offer a process for diagnosing or determining a susceptibility to cancers, autoimmune disease and related conditions through diagnosis by methods comprising determining from a sample derived from a subject an abnormally decreased or increased level of polypeptide or mRNA. This method of diagnosis is known as differential expression. The expression of a particular gene is compared between a diseased tissue and a normal tissue. A difference between the polynucleotide-related gene, mRNA, or protein in the two tissues is compared, for example in molecular weight, amino acid or nucleotide sequence, or relative abundance, indicates a change in the gene, or a gene which regulates it, in the tissue of the human that was suspected of being diseased.

Decreased or increased expression can be measured at the RNA level. PolyA RNA is first isolated from the two tissues and the detection of mRNA encoded by a gene corresponding to a differentially expressed polynucleotide of the invention can be detected by, for example, in situ hybridization in tissue sections, reverse trascriptase-PCR, using Northern blots containing poly A+ mRNA, or any other direct or indirect RNA detection method. An increased or decreased expression of a given RNA in a diseased tissue compared to a normal tissue suggests that the transcript and/or the expressed protein has a role in the disease. Thus detection of a higher or lower level of mRNA corresponding to SEQ ID NO: 1 relative to normal level is indicative of the presence of cancer in the patient.

mRNA expression levels in a sample can be determined by generation of a library of expressed sequence tags (ESTs) from the sample. The relative representation of ESTs in the library can be used to assess the relative representation of the gene transcript in the starting sample. The EST analysis of the test can then be compared to the EST analysis of a reference sample to determine the relative expression levels of the polynucleotide of interest.

Other mRNA analyses can be carried out using serial analysis of gene expression (SAGE) methodology (Velculescu et. Al. Science (1995) 270:484), differential display methodology (For example, U.S. Pat. No. 5,776,683) or hybridization analysis which relies on the specificity of nucleotide interactions.

Alternatively, the comparison could be made at the protein level. The protein sizes in the two tissues may be compared using antibodies to detect polypeptides in Western blots of protein extracts from the two tissues. Expression levels and subcellular localization may also be detected immunologically using antibodies to the corresponding protein. Further assay techniques that can be used to determine levels of a protein, such as a polypeptide of the present invention, in a sample derived from a host are well-known to those of skill in the art. A raised or decreased level of polypeptide expression in the diseased tissue compared with the same protein expression level in the normal tissue indicates that the expressed protein may be involved in the disease.

In the assays of the present invention, the diagnosis can be determined by detection of gene product expression levels encoded by at least one sequence set forth in SEQ ID NO: 1. A comparison of the mRNA or protein levels in a diseased versus normal tissue may also be used to follow the progression or remission of a disease.

A large number of polynucleotide sequences in a sample can be assayed using polynucleotide arrays. These can be used to examine differential expression of genes and to determine gene function. For example, arrays of the polynucleotide sequences SEQ ID NO:1 can be used to determine if any of the polynucleotides are differentially expressed between a normal and cancer cell. In one embodiment of the invention, an array of oligonucleotides probes comprising the SEQ ID NO:1 nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability (see for example: M. Chee et al., Science, Vol 274, pp 610-613 (1996)).

"Diagnosis" as used herein includes determination of a subject's susceptibility to a disease, determination as to whether a subject presently has the disease, and also the prognosis of a subject affected by the disease.

The present invention, further relates to a diagnostic kit for performing a diagnostic assay which comprises:
(a) a polynucleotide of the present invention, preferably the nucleotide sequence of SEQ ID NO: 1, or a fragment thereof;
(b) a nucleotide sequence complementary to that of (a), preferably the nucleotide sequence of SEQ ID NO: 6;
(c) a polypeptide of the present invention, preferably the polypeptide of SEQ ID NO: 2 or 3, or a fragment thereof; or
(d) an antibody to a polypeptide of the present invention, preferably to the polypeptide of SEQ ID NO:2 or 3.

The nucleotide sequences of the present invention are also valuable for chromosomal localisation. The sequence is specifically targeted to, and can hybridize with, a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found in, for example, V. McKusick, Mendelian Inheritance in Man (available on-line through Johns Hopkins University Welch Medical Library). The relationship between genes and diseases that have been mapped to the same chromosomal region are then identified through linkage analysis (coinheritance of physically adjacent genes). The differences in the cDNA or genomic sequence between affected and unaffected individuals can also be determined.

The polypeptides of the invention or their fragments or analogs thereof, or cells expressing them, can also be used as immunogens to produce antibodies immunospecific for polypeptides of the present invention. The term "immunospecific" means that the antibodies have substantially greater affinity for the polypeptides of the invention than their affinity for other related polypeptides in the prior art.

In a further aspect the invention provides an antibody immunospecific for a polypeptide according to the invention or an immunological fragment thereof as hereinbefore defined. Preferably the antibody is a monoclonal antibody.

Antibodies generated against polypeptides of the present invention may be obtained by administering the polypeptides or epitope-bearing fragments, analogs or cells to an animal, preferably a non-human animal, using routine protocols. For preparation of monoclonal antibodies, any technique which provides antibodies produced by continuous cell line cultures can be used. Examples include the hybridoma technique (Kohler, G. and Milstein, C., Nature (1975) 256:495-497), the trioma technique, the human B-cell hybridoma technique (Kozbor et al., Immunology Today (1983) 4:72) and the EBV-hybridoma technique (Cole et al., Monoclonal Antibodies and Cancer Therapy, 77-96, Alan R. Liss, Inc., 1985).

Techniques for the production of single chain antibodies, such as those described in U.S. Pat. No. 4,946,778, can also be adapted to produce single chain antibodies to polypeptides of this invention. Also, transgenic mice, or other organisms, including other mammals, may be used to express humanized antibodies.

The above-described antibodies may be employed to isolate or to identify clones expressing the polypeptide or to purify the polypeptides by affinity chromatography.

The antibody of the invention may also be employed to prevent or treat cancer, particularly colorectal cancer, autoimmune disease and related conditions.

Another aspect of the invention relates to a method for inducing or modulating an immunological response in a mammal which comprises inoculating the mammal with a polypeptide of the present invention, adequate to produce antibody and/or T cell immune response to protect or ameliorate the symptoms or progression of the disease. Yet another aspect of the invention relates to a method of inducing or modulating immunological response in a mammal which comprises, delivering a polypeptide of the present invention via a vector directing expression of the polynucleotide and coding for the polypeptide in vivo in order to induce such an immunological response to produce antibody to protect said animal from diseases.

It will be appreciated that the present invention therefore provides a method of treating abnormal conditions such as, for instance, cancer and autoimmune diseases, in particular, colorectal cancer, related to either a presence of, an excess of, or an under-expression of, CASB7439 polypeptide activity. Other abnormal conditions related to CASB7439 expression that the invention seeks to treat are chronic lymphocytic leukemiae and germ cell tumours.

The present invention further provides for a method of screening compounds to identify those which stimulate or which inhibit the function of the CASB7439 polypeptide. In general, agonists or antagonists may be employed for therapeutic and prophylactic purposes for such diseases as hereinbefore mentioned. Compounds may be identified from a variety of sources, for example, cells, cell-free preparations, chemical libraries, and natural product mixtures. Such agonists, antagonists or inhibitors so-identified may be natural or modified substrates, ligands, receptors, enzymes, etc., as the case may be, of the polypeptide; or may be structural or functional mimetics thereof (see Coligan et al., Current Protocols in Immunology 1(2): Chapter 5 (1991)). Screening methods will be known to those skilled in the art. Further screening methods may be found in for example D. Bennett et al., J Mol Recognition, 8:52-58 (1995); and K. Johanson et al., J Biol Chem, 270(16):9459-9471 (1995) and references therein.

Thus the invention provides a method for screening to identify compounds which stimulate or which inhibit the function of the polypeptide of the invention which comprises a method selected from the group consisting of:

(a) measuring the binding of a candidate compound to the polypeptide (or to the cells or membranes bearing the polypeptide) or a fusion protein thereof by means of a label directly or indirectly associated with the candidate compound;

(b) measuring the binding of a candidate compound to the polypeptide (or to the cells or membranes bearing the polypeptide) or a fusion protein thereof in the presence of a labeled competitior;

(c) testing whether the candidate compound results in a signal generated by activation or inhibition of the polypeptide, using detection systems appropriate to the cells or cell membranes bearing the polypeptide;

(d) mixing a candidate compound with a solution containing a polypeptide of claim 1, to form a mixture, measuring activity of the polypeptide in the mixture, and comparing the activity of the mixture to a standard; or (e) detecting the effect of a candidate compound on the production of mRNA encoding said polypeptide and said polypeptide in cells, using for instance, an ELISA assay.

The polypeptide of the invention may be used to identify membrane bound or soluble receptors, if any, through standard receptor binding techniques known in the art. Well known screening methods may also be used to identify agonists and antagonists of the polypeptide of the invention which compete with the binding of the polypeptide of the invention to its receptors, if any.

Thus, in another aspect, the present invention relates to a screening kit for identifying agonists, antagonists, ligands, receptors, substrates, enzymes, etc. for polypeptides of the present invention; or compounds which decrease or enhance the production of such to polypeptides, which comprises:

(a) a polypeptide of the present invention;
(b) a recombinant cell expressing a polypeptide of the present invention;
(c) a cell membrane expressing a polypeptide of the present invention; or
(d) antibody to a polypeptide of the present invention; which polypeptide is preferably that of SEQ ID NO:2 or 3.

It will be readily appreciated by the skilled artisan that a polypeptide of the present invention may also be used in a method for the structure-based design of an agonist, antagonist or inhibitor of the polypeptide, by:

(a) determining in the first instance the three-dimensional structure of the polypeptide;
(b) deducing the three-dimensional structure for the likely reactive or binding site(s) of an agonist, antagonist or inhibitor;
(c) synthesing candidate compounds that are predicted to bind to or react with the deduced binding or reactive site; and
(d) testing whether the candidate compounds are indeed agonists, antagonists or inhibitors.

Gene therapy may also be employed to effect the endogenous production of CASB7439 polypeptide by the relevant cells in the subject. For an overview of gene therapy, see Chapter 20, Gene Therapy and other Molecular Genetic-based Therapeutic Approaches, (and references cited therein) in Human Molecular Genetics, T Strachan and A P Read, BIOS Scientific Publishers Ltd (1996).

Vaccine preparation is generally described in Pharmaceutical Biotechnology, Vol. 61 Vaccine Design—the subunit and adjuvant approach, edited by Powell and Newman, Plenum Press, 1995. New Trends and Developments in Vaccines, edited by Voller et al., University Park Press, Baltimore, Md., U.S.A. 1978. Encapsulation within liposomes is described, for example, by Fullerton, U.S. Pat. No. 4,235,877. Conjugation of proteins to macromolecules is disclosed, for example, by Likhite, U.S. Pat. No. 4,372,945 and by Armor et al., U.S. Pat. No. 4,474,757.

The amount of protein in each vaccine dose is selected as an amount which induces an immunoprotective response without significant, adverse side effects in typical vaccinees. Such amount will vary depending upon which specific immunogen is employed. Generally, it is expected that each dose will comprise 1-1000 μg of protein, preferably 2-100 μg, most preferably 4-40 μg. An optimal amount for a particular vaccine can be ascertained by standard studies involving observation of antibody titres and other responses in subjects. Following an initial vaccination, subjects may receive a boost in about 4 weeks.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxyribonucleotide, which may be unmodified RNA or DNA or modified RNA or DNA including single and double stranded regions.

"Variant" refers to a polynucleotide or polypeptide that differs from a reference polynucleotide or polypeptide, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM *J. Applied Math.*, 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., Nucleic Acids Research 12(1): 387 (1984)), BLASTP, BLASTN, and FASTA (Atschul, S. F. et al., J. Molec. Biol. 215: 403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215: 403-410 (1990). The well known Smith Waterman algorithm may also be used to determine identity.

The preferred algorithm used is FASTA. The preferred parameters for polypeptide or polynucleotide sequence comparison using this algorithm include the following:
Gap Penalty: 12
Gap extension penalty: 4
Word size: 2, max 6
Preferred parameters for polypeptide sequence comparison with other methods include the following:
1) Algorithm: Needleman and Wunsch, J. Mol Biol. 48: 443-453 (1970)
Comparison matrix: BLOSSUM62 from Hentikoff and Hentikoff, Proc. Natl. Acad. Sci. USA. 89:10915-10919 (1992)
Gap Penalty: 12
Gap Length Penalty: 4
A program useful with these parameters is publicly available as the "gap" program from Genetics Computer Group, Madison Wis. The aforementioned parameters are the default parameters for polypeptide comparisons (along with no penalty for end gaps).

Preferred parameters for polynucleotide comparison include the following:
1) Algorithm: Needleman and Wunsch, J. Mol Biol. 48: 443-453 (1970)
Comparison matrix: matches=+10, mismatch=0
Gap Penalty: 50
Gap Length Penalty: 3
A program useful with these parameters is publicly available as the "gap" program from Genetics Computer Group, Madison Wis. The aforementioned parameters are the default parameters for polynucleotide comparisons.

By way of example, a polynucleotide sequence of the present invention may be identical to the reference sequence of SEQ ID NO:1, that is be 100% identical, or it may include up to a certain integer number of nucleotide alterations as compared to the reference sequence. Such alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in SEQ ID NO:1 by the numerical percent of the respective percent identity (divided by 100) and subtracting that product from said total number of nucleotides in SEQ ID NO:1, or:

$$n_n \leq x_n - (x_n \cdot y),$$

wherein $n_n$ is the number of nucleotide alterations, $x_n$ is the total number of nucleotides in SEQ ID NO:1, and y is, for instance, 0.70 for 70%, 0.80 for 80%, 0.85 for 85%, 0.90 for 90%, 0.95 for 95%, etc., and wherein any non-integer product of $x_n$ and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

Similarly, a polypeptide sequence of the present invention may be identical to the reference sequence of SEQ ID NO:2, that is be 100% identical, or it may include up to a certain integer number of amino acid alterations as compared to the reference sequence such that the % identity is less than 100%. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:2 by the numerical percent of the respective percent identity (divided by 100) and then subtracting that product from said total number of amino acids in SEQ ID NO:2, or:

$$n_a \leq x_a - (x_a \cdot y),$$

wherein $n_a$ is the number of amino acid alterations, $x_a$ is the total number of amino acids in SEQ ID NO:2, and y is, for instance 0.70 for 70%, 0.80 for 80%, 0.85 for 85% etc., and wherein any non-integer product of $x_a$ and y is rounded down to the nearest integer prior to subtracting it from $x_a$.

"Homolog" is a generic term used in the art to indicate a polynucleotide or polypeptide sequence possessing a high degree of sequence relatedness to a subject sequence. Such relatedness may be quntified by determining the degree of identity and/or similarity between the sequences being compared as hereinbefore described. Falling within this generic term are the terms "ortholog", meaning a polynucleotide or polypeptide that is the functional equivalent of a polynucleotide or polypeptide in another species and "paralog" meaning a functionally similar sequence when considered within the same species.

EXAMPLES

Example 1

Real-Time RT-PCR Analysis

Real-time RT-PCR (U. Gibson. 1996. Genome Research: 6,996) is used to compare mRNA transcript abundance of the candidate antigen in matched tumour and normal colon tissues from multiple patients. In addition, mRNA levels of the candidate gene in a panel of normal tissues are also evaluated by this approach.

Total RNA from normal and tumour colon is extracted from snap frozen biopsies using TriPure reagent (Boehringer). Total RNA from normal tissues is purchased from InVitrogen or is extracted from snap frozen biopsies using TriPure reagent. Poly-A+ mRNA is purified from total RNA after DNAase treatment using oligo-dT magnetic beads (Dynal). Quantification of the mRNA is performed by spectrofluorimetry (VersaFluor, BioRad) using SybrII dye (Molecular Probes). Primers for real-time PCR amplification are designed with the Perkin-Elmer Primer Express software using default options for TaqMan amplification conditions.

Real-time reactions are assembled according to standard PCR protocols using 2 ng of purified mRNA for each reaction. SybrI dye (Molecular Probes) is added at a final dilution of 1/75000 for real-time detection. Amplification (40 cycles) and real-time detection is performed in a Perkin-Elmer Biosystems PE7700 system using conventional instrument settings. Ct values are calculated using the PE7700 Sequence Detector software. Several Ct values are obtained for each samples: for the patient samples, the tumour Ct (CtT) and the matched normal colon Ct (CtN) values on the candidate TAA, and for the panel of normal tissue samples, a CtXY for each normal tissue XY. An another Ct (CtA) is also calculated on Actin gene, as an internal reference, for all of the samples. Alternatively, real-time PCR amplification can be monitored using a Taqman probe. Amplification (40 cycles) and real-time detection is performed in a Perkin-Elmer Biosystems PE7700 system using conventional instrument settings. Ct values are calculated using the PE7700 Sequence Detector Software. Ct values are obtained from each tissue sample for the target mRNA (CtX) and for the actin mRNA (CtA).

As the efficiency of PCR amplification under the prevailing experimental conditions is close to the theoretical amplification efficiency, $2^{(CtN/T/XY - CtA)}$ value is an estimate of the relative TAA transcript level of the sample, standardised with respect to Actin transcript level. A value of 1 thus suggests the candidate antigen and Actin have the same expression level.

Real-time PCR reactions were first performed on tumour colon and matching normal colon from biopsies of 12 patients. Reactions were then performed on a more complete data set totaling 18 patients (are included in this data set the first 12 patients). Duplicates for 6 out of these 18 patients were made in this data set. Six further patients were tested, and the results were pooled with the previous 18. The statistics on the final pool are shown in table 3, and illustrated in FIG. 1.

A series of 48 normal tissue samples, representing 29 different tissues, were also tested by the same procedure (analysed normal tissues are given in table 3). TAA transcript levels are calculated as described above. The proportion of patients over-expressing the candidate antigen, as well as the average transcript over-expression versus normal tissues is also calculated from this data set. The results are illustrated in FIG. 1.

TABLE 1

| CASB7439 Real-time PCR expression results: data set of 12 patients. | |
|---|---|
| % of patients with a mRNA level higher in matched tumour colon (positive patients) | 92% |
| % of patients with a mRNA level at least 3 fold higher in matched tumour colon | 92% |
| % of patients with a mRNA level at least 10 fold higher in matched tumour colon | 92% |
| % of patients with a mRNA level at least 3 fold lower in matched tumour colon. | 8% |
| Average matched normal colon mRNA level (Actin standardised) | 0.0026 |
| Average matched tumour colon mRNA level in positive patients (Actin standardised) | 0.265 |
| Average mRNA over-expression fold | 2028 |
| Median mRNA over-expression fold | 115 |
| Average normal tissues mRNA level | 0.0079 |
| Median normal tissues mRNA level | 0.0016 |
| Average normal tissues mRNA level | 0.0064 |
| Median normal tissues mRNA level | 0.0017 |
| % of patients with a mRNA level higher than average normal tissues | 92% |
| % of patients with a mRNA level higher than 10 fold average normal tissues | 75% |
| Normal non-dispensable tissues higher than median normal tissue mRNA level | None |

TABLE 2

| CASB7439 Real-time PCR expression results: data set of 18 patients. | |
|---|---|
| % of patients with a mRNA level higher in matched tumour colon (positive patients) | 89% |
| % of patients with a mRNA level at least 3 fold higher in matched tumour colon | 89% |
| % of patients with a mRNA level at least 10 fold higher in matched tumour colon | 78% |
| % of patients with a mRNA level at least 3 fold lower in matched tumour colon. | 5% |
| Average matched normal colon mRNA level (Actin standardised) | 0.005 |
| Average matched tumour colon mRNA level in positive patients (Actin standardised) | 0.152 |
| Average mRNA over-expression fold | 1100 |
| Median mRNA over-expression fold | 60 |
| Average normal tissues mRNA level | 0.0065 |
| Median normal tissues mRNA level | 0.0015 |
| Average normal tissues mRNA level | 0.005 |
| Median normal tissues mRNA level | 0.0015 |
| % of patients with a mRNA level higher than median normal tissues | 94% |
| % of patients with a mRNA level higher than 10 fold median normal tissues | 94% |
| Normal non-dispensable tissues higher than median normal tissue mRNA level | None |

TABLE 3

CASB7439 Real-time PCR expression results: data set of 24 patients

| | |
|---|---|
| % of patients with a CASB7439 transcript level higher in tumour colon than adjacent normal colon (positive patients) | 92% |
| % of positive patients with a CASB7439 transcript level at least 10 fold higher in tumour colon than adjacent normal colon | 75% |
| Average transcript over-expression fold in tumors of positive patients | 1289 |
| % of patients with a CASB7439 transcript level higher in tumour colon than normal tissue average | 96% |
| % of patients with a mRNA level at least 10 fold higher in tumour colon than normal tissue average | 62.5% |
| Normal tissues where CASB7439 transcript expression is equivalent to tumour transcript level in tumours | none |

Figure 2:
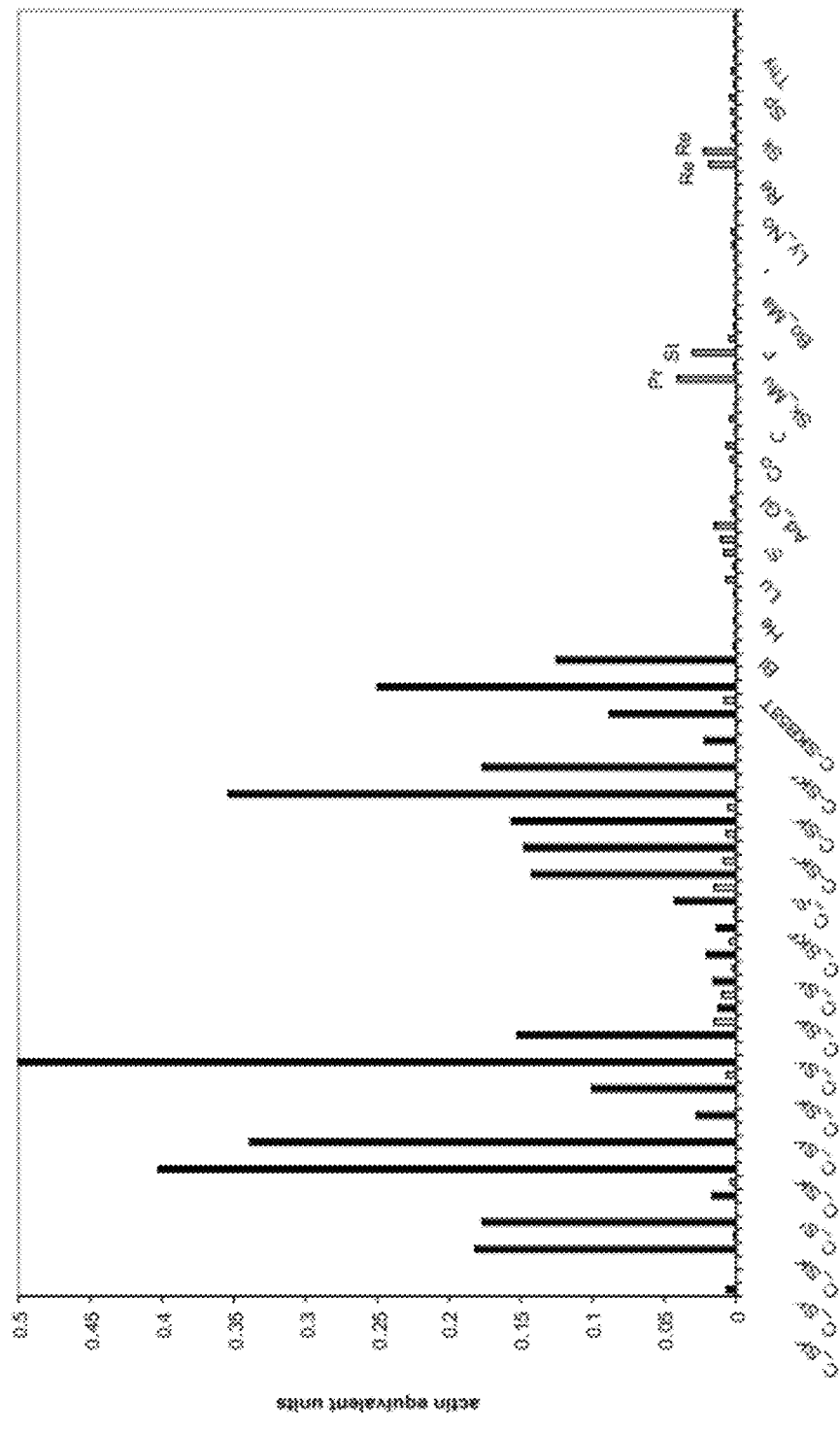

Real-time PCR reactions were also performed using the Taqman protocol (as described above) on tumour colon and adjacent normal colon from biopsies of 6 patients. Three replicate measures were taken for each, and the average was used for further calculations. Results are shown in FIG. 1. Moreover, 36 normal tissue samples, representing 28 different tissues (see table 5), were also tested by the same procedure. Results are shown in FIG. 2.

TABLE 4

CASB7439 Real-time PCR expression results using Taqman probe

| | |
|---|---|
| Number of tumor samples from different patients | 6 |
| % of patients with a CASB7439 transcript level higher in tumour colon than adjacent normal colon (positive patients) | 100% |
| % of positive patients with a CASB7439 transcript level at least 10 fold higher in tumour colon than adjacent normal colon | 83% |
| Average transcript over-expression fold in tumors of positive patients | 109 |
| % of patients with a CASB7439 transcript level higher in tumour colon than normal tissue average | 100% |
| % of patients with a mRNA level at least 10 fold higher in tumour colon than normal tissue average | 100% |
| Normal tissues where CASB7439 transcript expression is equivalent to tumour transcript level in tumours | none |

The results clearly suggest CASB7439 transcript is over-expressed in colorectal tumours compared to adjacent normal colon and to all of the above mentioned normal tissues. More than 90% of the patients strongly over-express CASB7439 transcript in tumour, as compared to adjacent normal colon. Average over-expression fold in the tumors is at least of 100. Moreover, more than 90% of the patients over-express the CASB7439 transcript in colorectal tumors as compared to other normal tissues, more than 60% of them over-expressing it at least 10 fold.

TABLE 5 listing of normal tissues used for CASB7439 transcript expression analysis.

| Tissue | Abbreviation |
|---|---|
| Adrenal gland | Ad_Gl |
| Aorta | Ao |
| Bladder | Bl |
| Bone marrow | Bo_Ma |
| Brain | Bra |
| Cervix | Ce |
| Colon | Co |
| Fallopian tube | Fa_Tu |
| Heart | He |
| Ileon | Il |
| Kidney | Ki |
| Liver | Li |
| Lung | Lu |
| Lymph node | Ly_No |
| Oesophagus | Oe |
| Parathyroid gland | Pa_Thy |
| Rectum | Re |
| Skin | Sk |
| Skeletal muscle | Sk_Mu |
| Small intestine | Sm_In |
| Spleen | Sp |
| Stomach | St |
| Thyroid gland | Thy |
| Trachea | Tra |
| Ovary | Ov |
| Placenta | Pl |
| Prostate | Pr |
| Testis | Te |

Example 2

Differential Screening of cDNA Arrays

Identification of tumour-associated genes in the subtracted cDNA library is accomplished by differential screening.

Total bacterial DNA is extracted from 100 μl over-night cultures. Bacteria are lysed with guanidium isothiocyantate and the bacterial DNA is affinity purified using magnetic glass (Boehringer). Plasmid inserts are recovered from the bacterial DNA by Advantage PCR amplification (Clontech). The PCR products are dotted onto two nylon membranes to produce high density cDNA arrays using the Biomek 96 HDRT tool (Beekman). The spotted cDNA is covalently linked to the membrane by UV irradiation. The first membrane is hybridised with a mixed cDNA probe prepared from the tumour of a single patient. The second membrane is hybridised with an equivalent amount of mixed cDNA probe prepared from normal colon of the same patient. The probe cDNA is prepared by PCR amplification as described above and is labelled using the AlkPhos Direct System (Amersham). Hybridisation conditions and stringency washes are as described in the AlkPhos Direct kit. Hybridized probe is detected by chemiluminescence. Hybridisation intensities for each cDNA fragment on both blots are measured by film densitometry or direct measurement (BioRad Fluor-S Max). The ratio of the tumour to normal hybridisation intensities (T/N) is calculated for each gene to evaluate the degree of over-expression in the tumour. Genes which are significantly over-expressed in colon tumours are followed-up. Significance is arbitrarily defined as one standard deviation of the T/N frequency distribution. Differential screening experiments are repeated using RNA from multiple patient donors (>18) to estimate the frequency of over-expressing tumours in the patient population. In addition, the DNA arrays are hybridised with mixed cDNA probes from normal tissues other than colon (see list above) to determine the level of expression of the candidate gene in these tissues.

Example 3

DNA Microarrays

DNA micro-arrays are used to examine mRNA expression profiles of large collections of genes in multiple samples. This information is used to complement the data obtained by real-time PCR and provides an independent measure of gene expression levels in tumors and normal tissues.

Examples of current technologies for production of DNA micro-arrays include 1) The Affymetrix "GeneChip" arrays in which oligonucleotides are synthetized on the surface of the chip by solid phase chemical synthesis using a photolithographic process 2) DNA spotting technology in which small volumes of a DNA solution are robotically deposited and then immobilized onto the surface of a solid phase (e.g. glass). In both instances, the chips are hybridized with cDNA or cRNA which has been extracted from the tissue of interest (e.g. normal tissue, tumour etc. . . . ) and labeled with radioactivity or with a fluorescent reporter molecule. The labeled material is hybridized to the chip and the amount of probe bound to each sequence on the chip is determined using a specialized scanner. The experiment can be set-up with a single fluorescent reporter (or radioactivity) or, alternatively, can be performed using two fluorescent reporters. In this latter case, each of the two samples is labeled with one of the reporter molecules. The two labeled samples are then hybridized competitively to the sequences on the DNA chip. The ratio of the two fluorescent signals is determined for each sequence on the chip. This ratio is used to calculate the relative abundance of the transcript in the two samples. Detailed protocols are available from a number of sources including "DNA Microarrays: A practical approach. Schena M. Oxford University Press 1999" and the World Wide Web found by following the address "cmgm.stanford.edu/gbrown/protocols/index.html", or "arrayit.com/DNA-Microarray-Protocols/" and specialized distributors (e.g. Affymetrix).

Example 5

Northern-Southern Blot Analysis

Limited amounts of mixed tumour and matched normal colon cDNA are amplified by Advantage PCR (see above). Messenger RNA from multiple normal tissues is also amplified using the same procedure. The amplified cDNA (1 µg) is electrophoresed on a 1.2% agarose gel and transferred onto a nylon membrane. The membrane is hybridised (AlkPhos Direct System) with a probe prepared using a fragment of the candidate TAA cDNA. Northern-Southern analysis provides information on transcript size, presence of splice variants and transcript abundance in tumour and normal tissues.

Example 6

Northern Blot Analysis

Northern blots are produced according to standard protocols using 1 ng of poly A+ mRNA. Radioactive probes are prepared using the Ready-to-Go system (Pharmacia).

Example 7

Experimental Identification of the Full Length cDNA Sequence

Colon tumour cDNA libraries are constructed using the Lambda Zap II system (Stratagene) from 5 µg of polyA+ mRNA. The supplied protocol is followed except that SuperscriptII (Life Technologies) is used for the reverse transcription step. Oligo dT-primed and random-primed libraries are constructed. About $1.5 \times 10^6$ independent phages are plated for each screening of the library. Phage plaques are transferred onto nylon filters and hybridised using a cDNA probe labelled with AlkPhos Direct. Positive phages are detected by chemiluminescence. Positive phage are excised from the agar plat, eluted in 500 µl SM buffer and confirmed by gene-specific PCR. Eluted phages are converted to single strand M13 bacteriophage by in vivo excision. The bacteriophage is then converted to double strand plasmid DNA by infection of E. coli. Infected bacteria are plated and submitted to a second round of screening with the cDNA probe. Plasmid DNA is purified from positive bacterial clones and sequenced on both strands.

When the full length gene cannot be obtained directly from the cDNA library, missing sequence is isolated using RACE technology (Marathon Kit, ClonTech.). This approach relies on reverse transcribing mRNA into double strand cDNA, ligating linkers onto the ends of the cDNA and amplifying the desired extremity of the cDNA using a gene-specific primer and one of the linker oligonucleotides. Marathon PCR products are cloned into a plasmid (pCRII-TOPO, InVitrogen) and sequenced.

The polynucleotide of SEQ ID NO:1 was obtained using this procedure.

Example 8

EST Profiles

A complementary approach to experimental antigen tissue expression characterization is to explore the human EST database. ESTs ('Expressed Sequence Tags') are small fragments of cDNA made from a collection of mRNA extracted from a particular tissue or cell line. Such database currently provides a massive amount of human ESTs ($2 \cdot 10^6$) from several thousands of cDNA tissue libraries, including tumoral tissues from various types and states of disease. By means of informatics tools (Blast), a comparison search of the CASB7439 sequence is performed in order to have further insight into tissue expression.

| EST distribution of CASB7439: | |
|---|---|
| EST GenBank Accession number | EST cDNA tissue library |
| C00634 | Human adult (K. Okubo) |
| AA468668 | NCI_CGAP_Co3 |
| AA565752 | NCI_CGAP_Co11 |
| AA565766 | NCI_CGAP_Co11 |
| AA565767 | NCI_CGAP_Co11 |
| AI337239 | NCI_CGAP_Co16 |
| AI337448 | NCI_CGAP_Co16 |
| AI393930 | NCI_CGAP_CLL1 |
| AI473673 | NCI_CGAP_Co14 |
| AI632444 | NCI_CGAP_GC6 |
| AI861937 | NCI_CGAP_Co16 |
| AI825214 | NCI_CGAP_GC6 |
| AW080652 | NCI_CGAP_Co19 |
| AW083899 | NCI_CGAP_Co19 |
| AW206058 | NCI_CGAP_Sub3 |
| AW237006 | NCI_CGAP_GC6 |
| AW364626 | DT0036 |
| AW449612 | NCI_CGAP_Sub5 |

These ESTs match perfectly with CASB7439. The list contains 9 ESTs from 4 different tumor colon libraries, one EST from one normal colon library, 3 ESTs from one tumor germ cell library, one EST from one chronic lymphocyte leukemia cells library, 2 ESTs from 2 mixed tumors libraries, 2 ESTs from libraries of unknown type. This clearly suggests, as expected, that CASB7439 is over-expressed in tumor tissues, with an emphasis in colorectal tumor tissues, as compared to normal tissues.

Example 9

9.1 Expression and Purification of Tumour-Specific Antigens

Expression in microbial hosts, or alternatively in vitro transcription/translation, is used to produce the antigen of the invention for vaccine purposes and to produce protein fragments or whole protein for rapid purification and generation of antibodies needed for characterization of the naturally expressed protein by immunohistochemistry or for follow-up of purification.

Recombinant proteins may be expressed in two microbial hosts, *E. coli* and in yeast (such as *Saccharomyces cerevisiae* or *Pichia pastoris*). This allows the selection of the expression system with the best features for this particular antigen production. In general, the recombinant antigen will be expressed in *E. coli* and the reagent protein expressed in yeast.

The expression strategy first involves the design of the primary structure of the recombinant antigen. In general an expression fusion partner (EFP) is placed at the N terminal extremity to improve levels of expression that could also include a region useful for modulating the immunogenic properties of the antigen, an immune fusion partner (IFP). In addition, an affinity fusion partner (AFP) useful for facilitating further purification is included at the C-terminal end.

As mentioned above, several constructs might undergo comparative evaluation: For rapid expression and purification as well as generation of antibodies against CASB7439, it is proposed to generate in *E. Coli* a full length CASB7439 protein with NS1 as EFP and a histidine tail as AFP.

Therefore, two constructs are proposed:

Construct 1:
Full length wild type CASB7439 cDNA in fusion with NS1 cDNA as EFP and with a histidine tail coding cDNA as an AFP (SEQ ID NO:8). The encoded fusion protein sequence is SEQ ID NO:10.

Construct 2:
Full length mutated CASB7439 cDNA in fusion with NS1 cDNA as EFP and with a histidine tail coding cDNA as an AFP (SEQ ID NO:9). It is proposed in this construct to have the first 50 codons of native CASB7439 cDNA replaced by codons specific of the *E. coli* codon usage, to enhance expression potential of CASB7439 in its *E. coli* host. The encoded fusion protein sequence is SEQ ID NO:10.

The CASB7439 protein design is as shown below:

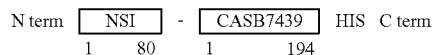

"NS1" is the N-terminal fragment (80 amino acids) of the Influenza protein NS1. "HIS" is a polyhistidine tail.

The recombinant strain used is AR58: a cryptic λ lysogen derived from N99 that is gal E::Tn 10,Δ-8(chlD-pgl)Δ-H1 (cro-chlA), N⁺, and cI857 (Proc. Natl. Acad. Sci. USA vol 82, pp. 88-92, January 1985 Biochemistry)

When the recombinant strains are available, the recombinant product is characterized by the evaluation of the level of expression and the prediction of further solubility of the protein by analysis of the behavior in the crude extract.

After growth on appropriate culture medium and induction of the recombinant protein expression, total extracts are analyzed by SDS-PAGE. The recombinant proteins are visualized in stained gels and identified by Western blot analysis using specific antibodies.

Plasmid:

| | |
|---|---|
| name: TCM 281 | pRIT . . . 15143 |
| replicon: pMB1 | |
| selection: Kan | |
| promotor: PL long | |
| insert: NS1-C74-39-His | |

Expression of the Recombinant Protein from Construct 1:

Bacteria was grown in LB medium+50 μg/ml Kan at 30° C.

When the culture reached OD=0.5 (620 nm), the culture was heated up to 39° C., after 5 hours of induction, cells were harvested Extract Preparation:

| | |
|---|---|
| Cell concentration: | .50× . . . in buffer PBS + complete . . . |
| Disruption: | press french 3× |
| Centrifugation: | 30 min at 14000 t |
| Comment: | >90% in the supernatant of cellular extract |

Figure 3:
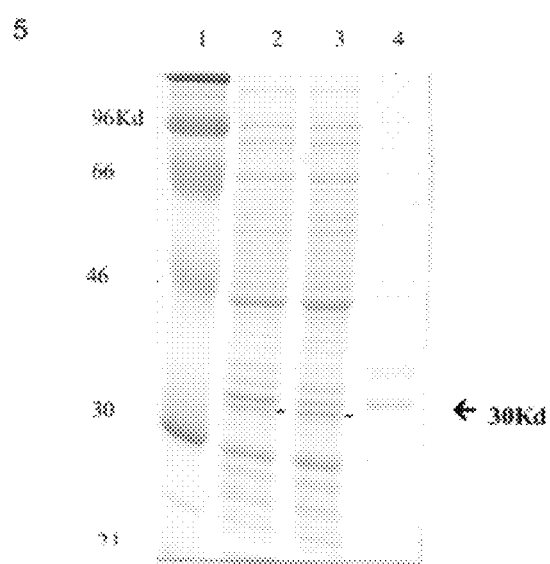
Figure 4:
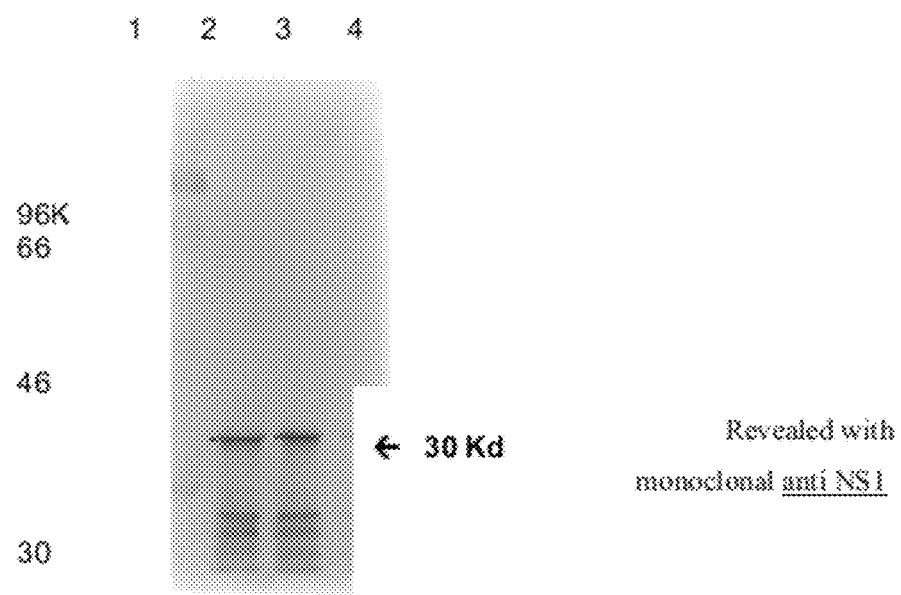

The cell extract was run on a 12.5% SDS PAGE, and subsequently stained with Coomassie blue. A Western blot was also performed using an commercial monoclonal antibody against the poly-histidine tail (Quiagen). The resulting gels (FIGS. 3 and 4), show that the protein is expressed, and visible in the cell extract supernatant.

The purification scheme follows a classical approach based on the presence of an His affinity tail in the recombinant protein. In a typical experiment the disrupted cells are filtered and the acellular extracts loaded onto an Ion Metal Affinity Chromatography (IMAC; Ni⁺⁺ NTA from Qiagen) that will specifically retain the recombinant protein. The retained proteins are eluted by 0-500 mM imidazole gradient (possibly in presence of a detergent) in a phosphate buffer.

The supernatant from the harvested culture was denatured in 6M urea, 100 mM NaH₂PO₄, 10 mM Tris, PH 8, and loaded on a chromatographic column IMAC Qiagen NTA Ni⁺⁺ under the following conditions:

| Equilibration buffer: | NaH2Po4 | 100 mM | PH 8 |
|---|---|---|---|
| | Tris | 10 mM | |
| | Urea | 6M | |

Sample: supernatant in urea 6M, 100 mM NaH2PO4, 10 mM Tris

| Wash buffers: | 1)NaH2PO4 | 100 mM | PH 8 |
|---|---|---|---|
| | Tris | 10 mM | |
| | urea | 6M | |
| | Imidazole | 25 mM | |

-continued

| | | | |
|---|---|---|---|
| 2)NaH2Po4 | 100 mM | PH8 | |
| Tris | 10 mM | | |
| Urea | 6 mM | | |
| Imidazole | 50 mM | | |

| | | | | |
|---|---|---|---|---|
| Elution buffer: | NaH2PO4 | 100 mM | PH 5.5 | |
| | Tris | 10 mM | | |
| | Urea | 6M | | |
| | Imidazole | 500 mM | | |

Figure 5:
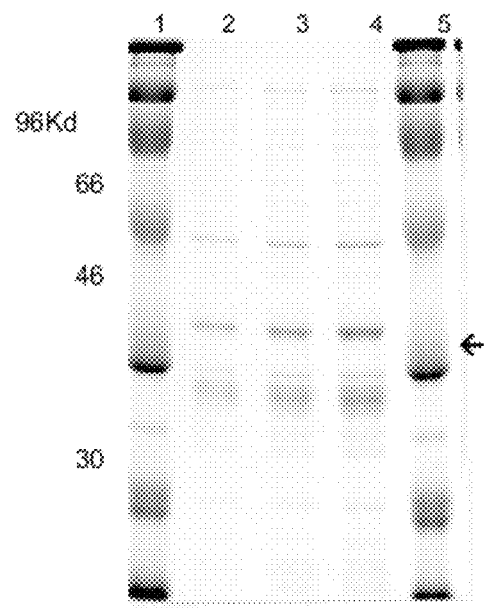
Figure 6:
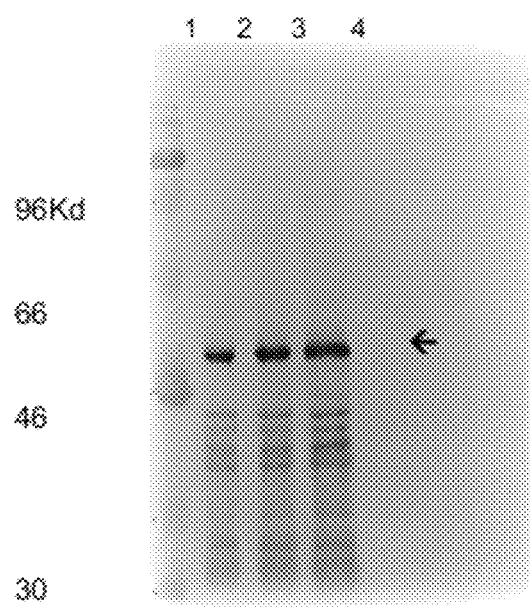
FIG. 6 shows a Western blot CASB7439 after purification as revealed by an anti-polyhistidine monoclonal antibody.
Figure 7:
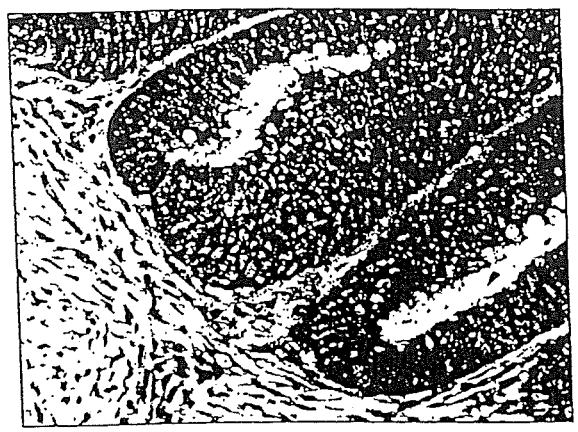
FIG. 7 shows IHC results on colon tumour #9476 biospy.
Figure 8:
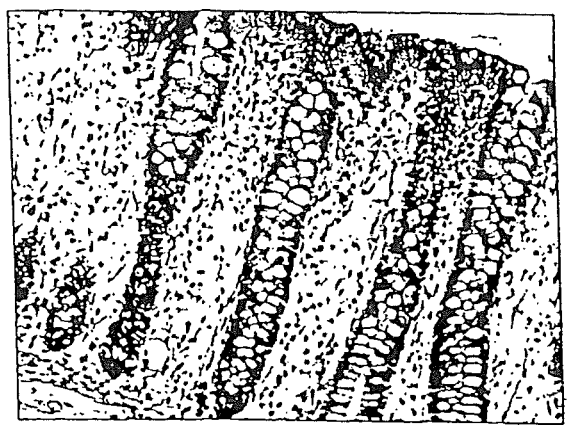
FIG. 8 shows IHC results colon normal mucosa #9476 biospy.

The eluted protein in 500 mM imidazole+6M urea is dialysed under the following conditions:
PBS PH 7.2+sarkosyl 0.5%+4M urea
idem at 2M urea 2 hrs
idem at 0M urea 2 hrs The final material is freezed and stored. The protein content was quantified using a Lowry protein assay (0.9 mg/1.2 ml). The purity was assessed by a 12.5% PAGE SDS stained with Coomassie blue (FIG. 5), and the presence of the recombinant protein was checked by Western blot, using a anti-polyhistidine monoclonal antibody (FIG. 6)

A comparative evaluation of the different versions of the expressed antigen will allow the selection of the most promising candidate that is to be used for further purification and immunological evaluation.

9.2 Antibody Production and Immunohistochemistry

Small amounts of relatively purified protein can be used to generate immunological tools in order to
a) detect the expression by immunohistochemistry in normal or cancer tissue sections;
b) detect the expression, and to follow the protein during the purification process (ELISA/Western Blot); or
c) characterise/quantify the purified protein (ELISA).

9.2.1 Polyclonal Antibodies:
Immunization

Rabbits are immunised, intramuscularly (I.M.), 3 times at 3 weeks intervals with 100 μg of protein, formulated in the adjuvant 3D-MPL/QS21. Three weeks after each immunisation a blood sample is taken and the antibody titer estimated in the serum by ELISA using the protein as coating antigen following a standard protocol.

ELISA 96 well microplates (maxisorb Nunc) are coated with 5 μg of protein overnight at 4° C. After 1 hour saturation at 37° C. with PBS NCS 1%, serial dilution of the rabbit sera is added for 1H 30 at 37° C. (starting at 1/10). After 3 washings in PBS Tween, anti rabbit biotinylated anti serum (Amersham)) is added (1/5000). Plates are washed and peroxydase coupled streptavidin (1/5000) is added for 30 min at 37° C. After washing, 50 μl TMB (BioRad) is added for 7 min and the reaction then stopped with H2SO4 0.2M. The OD can be measured at 450 nm and midpoint dilutions calculated by SoftmaxPro.

9.2.2 Monoclonal Antibodies:
Immunization

5 BALB/c mice are immunized 3 times at 3 week intervals with 5 μg of purified protein. Bleedings are performed 14 days post II and 1 week post 3. The sera are tested by Elisa on purified protein used as coated antigen. Based on these results (midpoint dilution>10000) one mouse is selected for fusion.

Fusion/HAT Selection

Spleen cells are fused with the SP2/0 myeloma according to a standard protocol using PEG 40% and DMSO 5%. Cells are then seeded in 96 well plates 2.5×104-105 cells/well and resistant clones will be selected in HAT medium. The supernatant of these hybridomas will be tested for their content in specific antibodies and when positive, will be submitted to 2 cycles of limited dilution. After 2 rounds of screening, 3 hybridomas will be chosen for ascitis production.

9.2.3 Immunohistochemistry

When antibodies are available, immuno staining is performed on normal or cancer tissue sections, in order to determine:
the level of expression of the antigen of the invention in cancer relative to normal tissue or
the proportion of cancer of a certain type expressing the antigen
if other cancer types also express the antigen
the proportion of cells expressing the antigen in a cancer tissue Tissue Sample Preparation After dissection, the tissue sample is mounted on a cork disk in OCT compound and rapidly frozen in isopentane previously super cooled in liquid nitrogen (−160° C.). The block will then be conserved at −70° C. until use. 7-10 nm sections will be realised in a cryostat chamber (−20, −30° C.).

Staining

Tissue sections are dried for 5 min at room Temperature (RT), fixed in acetone for 10 min at RT, dried again, and saturated with PBS 0.5% BSA 5% serum. After 30 min at RT either a direct or indirect staining is performed using antigen specific antibodies. A direct staining leads to a better specificity but a less intense staining whilst an indirect staining leads to a more intense but less specific staining.

9.3 Analysis of Human Cellular Immune Responses to the Antigen of the Invention The immunological relevance of the antigen of the invention can be assessed by in vitro priming of human T cells. All T cell lymphocyte lines and dendritic cells are derived from PBMCs (peripheral blood mononuclear cells) of healthy donors (preferred HLA-A2 subtype). An HLA-A2.1/Kb transgenic mouse model is also used for screening of HLA-A2.1 peptides.

Newly discovered antigen-specific CD8$^+$ T cell lines are raised and maintained by weekly in vitro stimulation. The lytic activity and the γ-IFN production of the CD8$^+$ lines in response to the antigen or antigen derived-peptides is tested using standard procedures.

Two strategies to raise the CD8$^+$ T cell lines are used: a peptide-based approach and a whole gene-based approach. Both approaches require the full-length cDNA of the newly discovered antigen in the correct reading frame to be either cloned in an appropriate delivery system or to be used to predict the sequence of HLA binding peptides.

Peptide-Based Approach

Briefly, transgenic mice are immunized with adjuvanted HLA-A2 peptides, those unable to induce a CD8$^+$ response (as defined by an efficient lysis of peptide-pulsed autologous spleen cells) will be further analyzed in the human system.

Human dendritic cells (cultured according to Romani et al.) will be pulsed with peptides and used to stimulate CD8$^+$-sorted T cells (by Facs). After several weekly stimulations, the CD8$^+$ lines will be first tested on peptide-pulsed autologous BLCL (EBV-B transformed cell lines). To verify the proper in vivo processing of the peptide, the CD8$^+$ lines will be tested on cDNA-transfected tumour cells (HLA-A2 transfected LnCaP, Skov3 or CAMA tumour cells).

Whole Gene-Based Approach

CD8+ T cell lines will be primed and stimulated with either gene-gun transfected dendritic cells, retrovirally transduced B7.1-transfected fibroblasts, recombinant pox virus or adenovirus infected dendritic cells. Virus infected cells are very efficient to present antigenic peptides since the antigen is expressed at high level but can only be used once to avoid the over-growth of viral T cells lines.

After alternated stimulations, the CD8+ lines are tested on cDNA-transfected tumour cells as indicated above. Peptide specificity and identity is determined to confirm the immunological validation.

CD4+ T-Cell Response

Similarly, the CD4+ T-cell immune response can also be assessed. Generation of specific CD4+ T-cells is made using dendritic cells loaded with recombinant purified protein or peptides to stimulate the T-cells.

Predicted Epitopes (Nonamers and Decamers) Binding HLA Alleles:

The HLA Class I binding peptide sequences are predicted either by the Parker's algorithm (Parker, K. C., M. A. Bednarek, and J. E. Coligan. 1994. Scheme for ranking potential HLA-A2 binding peptides based on independent binding of individual peptide side-chains. J. Immunol. 152:163 and found by following the address "bimas.dcrt.nih.gov/molbio/hla_bind/" or the Rammensee method (Rammensee, Friede, Stevanovic, MHC ligands and peptide motifs: 1st listing, Immunogenetics 41, 178-228, 1995; Rammensee, Bachmann, Stevanovic: MHC ligands and peptide motifs. Landes Bioscience 1997, and found by following the address "134.2.96.221/scripts/hlaserver.dll/home.htm". Peptides are then screened in the HLA-A2.1/Kb transgenic mice model (Vitiello et al.).

The HLA Class II binding peptide sequences are predicted using the Tepitope algorithm, with a score cut-offset to 6 (Sturniolo, Hammer at al., Nature Biotechnology. 1999. 17; 555-561).

The following tables gather the Class I and II predicted epitope sequences:

HLA-A 0201: decamers

| Rank | Start Position | Subsequence Residue Listing | Parker's Score° | SEQ ID: |
|---|---|---|---|---|
| 1 | 64 | KLVNLGFQAL | 142.060 | SEQ ID NO: 16 |

°Estimate of Half Time of Disassociation of a Molecule Containing This Subsequence.

HLA-A 0201: nonamers

| Rank | Start Position | Subsequence Residue Listing | Parker's Score° | SEQ ID: |
|---|---|---|---|---|
| 1 | 182 | ELLDFSSWL | 507.976 | SEQ ID NO: 17 |
| 2 | 104 | RLLAEHDAV | 126.098 | SEQ ID NO: 18 |
| 3 | 64 | KLVNLGFQA | 100.850 | SEQ ID NO: 19 |

°Estimate of Half Time of Disassociation of a Molecule Containing This Subsequence.

HLA-A 24: nonamers

| Rank | Start Position | Subsequence Residue Listing | Parker's Score | SEQ ID: |
|---|---|---|---|---|
| 1 | 97 | EYIRALQRL | 360.000 | SEQ ID NO: 20 |

°Estimate of Half Time of Disassociation of a Molecule Containing This Subsequence.

HLA-A 24: decamers

| Rank | Start Position | Subsequence Residue Listing | Parker's Score | SEQ ID: |
|---|---|---|---|---|
| 1 | 97 | EYIRALQRLL | 360.000 | SEQ ID NO: 21 |

°Estimate of Half Time of Disassociation of a Molecule Containing This Subsequence.

HLA-B 7: decamers

| Rank | Start Position | Subsequence Residue Listing | Parker's Score | SEQ ID: |
|---|---|---|---|---|
| 1 | 111 | AVRNALAGGL | 600.000 | SEQ ID NO: 22 |

°Estimate of Half Time of Disassociation of a Molecule Containing This Subsequence.

HLA-B 4403: decamers

| Rank | Start Position | Subsequence Residue Listing | Parker's Score | SEQ ID: |
|---|---|---|---|---|
| 1 | 156 | SEPGSPRSAY | 360.000 | SEQ ID NO: 23 |
| 2 | 89 | VETLRSAVEY | 180.000 | SEQ ID NO: 24 |

°: Estimate of Half Time of Disassociation of a Molecule Containing This Subsequence.

HLA-DRB1*1501: nonamers

| Rank | Start Position | Subsequence Residue Listing | Tepitope Score | SEQ ID: |
|---|---|---|---|---|
| 1 | 99 | IRALQRLLA | 5.6 | SEQ ID NO: 25 |

HLA-DRB1*1502: nonamers

| Rank | Start Position | Subsequence Residue Listing | Tepitope Score | SEQ ID: |
|---|---|---|---|---|
| 1 | 99 | IRALQRLLA | 4.6 | SEQ ID NO: 25 |

HLA-DRB1*0402: nonamers

| Rank | Start Position | Subsequence Residue Listing | Tepitope Score | SEQ ID: |
|---|---|---|---|---|
| 1 | 120 | LRPQAVRPS | 5.4 | SEQ ID NO: 26 |

HLA-DRB1*1101: nonamers

| Rank | Start Position | Subsequence Residue Listing | Tepitope Score | SEQ ID: |
|---|---|---|---|---|
| 1 | 99 | IRALQRLLA | 4.8 | SEQ ID NO: 25 |

HLA-DRB1*1102: nonamers

| Rank | Start Position | Subsequence Residue Listing | Tepitope Score | SEQ ID: |
|---|---|---|---|---|
| 1 | 99 | LRPQAVRPS | 6.2 | SEQ ID NO: 26 |

HLA-DRB1*1104: nonamers

| Rank | Start Position | Subsequence Residue Listing | Tepitope Score | SEQ ID: |
|---|---|---|---|---|
| 1 | 99 | IRALQRLLA | 5.8 | SEQ ID NO: 25 |

HLA-DRB1*1106: nonamers

| Rank | Start Position | Subsequence Residue Listing | Tepitope Score | SEQ ID: |
|---|---|---|---|---|
| 1 | 99 | IRALQRLLA | 5.8 | SEQ ID NO: 25 |

HLA-DRB1*1301: nonamers

| Rank | Start Position | Subsequence Residue Listing | Tepitope Score | SEQ ID: |
|---|---|---|---|---|
| 1 | 120 | LRPQAVRPS | 6.6 | SEQ ID NO: 26 |
| 2 | 73 | LRQHVPHGG | 4.9 | SEQ ID NO: 27 |
| 3 | 31 | LLRCSRRRR | 4.4 | SEQ ID NO: 33 |

HLA-DRB1*1302: nonamers

| Rank | Start Position | Subsequence Residue Listing | Tepitope Score | SEQ ID: |
|---|---|---|---|---|
| 1 | 120 | LRPQAVRPS | 5.6 | SEQ ID NO: 26 |

HLA-DRB1*1304: nonamers

| Rank | Start Position | Subsequence Residue Listing | Tepitope Score | SEQ ID: |
|---|---|---|---|---|
| 1 | 120 | LRPQAVRPS | 6.2 | SEQ ID NO: 26 |
| 2 | 73 | LRQHVPHGG | 4.8 | SEQ ID NO: 27 |
| 3 | 31 | LGFQALRQH | 4.6 | SEQ ID NO: 28 |

HLA-DRB1*1305: nonamers

| Rank | Start Position | Subsequence Residue Listing | Tepitope Score | SEQ ID: |
|---|---|---|---|---|
| 1 | 99 | IRALQRLLA | 4.8 | SEQ ID NO: 25 |

HLA-DRB1*0703: nonamers

| Rank | Start Position | Subsequence Residue Listing | Tepitope Score | SEQ ID: |
|---|---|---|---|---|
| 1 | 112 | VRNALAGGL | 5.1 | SEQ ID NO: 29 |
| 2 | 98 | YIRALQRLL | 4.8 | SEQ ID NO: 30 |
| 3 | 65 | LVNLGFQAL | 4.5 | SEQ ID NO: 31 |

HLA-DRB5*0101: nonamers

| Rank | Start Position | Subsequence Residue Listing | Tepitope Score | SEQ ID: |
|---|---|---|---|---|
| 1 | 96 | VEYIRALQR | 4.3 | SEQ ID NO: 32 |

Example 10

CASB7439 Specific Cellular Immune Response

A further way of assessing CASB7439 immunogenicity is to demonstrate CASB7439 antigen has a potential to trigger a cellular immune response. For that purpose, it has to be verified the human CD4+ T-cell repertoire has the ability to recognise CASB7439 antigens presented by APC's (antigen-presenting cells) in a MHC class II restricted manner.

To demonstrate CASB7439 antigen can generate a specific CD4+ T-cell activity in human, as well as to identify CASB7439 epitopes, a series of "in vitro priming" experiments have been carried out with the PBMC's of three healthy donors.

In Vitro Priming of Donor #1

In-vitro priming cultures with the PBMC of donor #1 were established using 15-mer peptides overlapping by 11 amino acids from the sequence of CASB7439.

CD4 Peptide Table

| Peptide No. | Sequence | Amino Acids | Pool | SEQ ID NO. |
|---|---|---|---|---|
| 1 | MDGGTLPRSAPPAPP | 1-15 | 1 | 34 |
| 2 | TLPRSAPPAPPVPVG | 5-19 | 1 | 35 |
| 3 | SAPPAPPVPVGCAAR | 9-23 | 1 | 36 |
| 4 | APPVPVGCAARRRPA | 13-27 | 1 | 37 |
| 5 | PVGCAARRRPASPEL | 17-31 | 1 | 38 |
| 6 | AARRRPASPELLRCS | 21-35 | 1 | 39 |
| 7 | RPASPELLRCSRRRR | 25-39 | 1 | 40 |
| 8 | PELLRCSRRRRPATA | 29-43 | 2 | 41 |
| 9 | RCSRRRRPATAETGG | 33-47 | 2 | 42 |
| 10 | RRRPATAETGGGAAA | 37-51 | 2 | 43 |
| 11 | ATAETGGGAAAVARR | 41-55 | 2 | 44 |
| 12 | TGGGAAAVARRNERE | 45-59 | 2 | 45 |
| 13 | AAAVARRNERERNRV | 49-63 | 2 | 46 |
| 14 | ARRNERERNRVKLVN | 53-67 | 2 | 47 |
| 15 | ERERNRVKLVNLGFQ | 57-71 | 3 | 48 |
| 16 | NRVKLVNLGFQALRQ | 61-75 | 3 | 49 |
| 17 | LVNLGFQALRQHVPH | 65-79 | 3 | 50 |
| 18 | GFQALRQHVPHGGAS | 69-83 | 3 | 51 |
| 19 | LRQHVPHGGASKKLS | 73-87 | 3 | 52 |
| 20 | VPHGGASKKLSKVET | 77-91 | 3 | 53 |
| 21 | GASKKLSKVETLRSA | 81-95 | 3 | 54 |
| 22 | KLSKVETLRSAVEYI | 85-89 | 4 | 55 |
| 23 | VETLRSAVEYIRALQ | 89-103 | 4 | 56 |
| 24 | RSAVEYIRALQRLLA | 93-107 | 4 | 57 |
| 25 | EYIRALQRLLAEHDA | 97-111 | 4 | 58 |
| 26 | ALQRLLAEHDAVRNA | 101-115 | 4 | 59 |
| 27 | LLAEHDAVRNALAGG | 105-119 | 4 | 60 |
| 28 | HDAVRNALAGGLRPQ | 109-123 | 5 | 61 |
| 29 | RNALAGGLRPQAVRP | 113-127 | 5 | 62 |
| 30 | AGGLRPQAVRPSAPR | 117-131 | 5 | 63 |
| 31 | RPQAVRPSAPRGPPG | 121-135 | 5 | 64 |
| 32 | VRPSAPRGPPGTTPV | 125-139 | 5 | 65 |
| 33 | APRGPPGTTPVAASP | 129-143 | 5 | 66 |
| 34 | PPGTTPVAASPSRAS | 133-147 | 6 | 67 |
| 35 | TPVAASPSRASSSPG | 137-151 | 6 | 68 |
| 36 | ASPSRASSSPGRGGS | 141-155 | 6 | 69 |
| 37 | RASSSPGRGGSSEPG | 145-159 | 6 | 70 |
| 38 | SPGRGGSSEPGSPRS | 149-163 | 6 | 71 |
| 39 | GGSSEPGSPRSAYSS | 153-167 | 6 | 72 |
| 40 | EPGSPRSAYSSDDSG | 157-171 | 7 | 73 |
| 41 | PRSAYSSDDSGCEGA | 161-175 | 7 | 74 |
| 42 | YSSDDSFCEGALSPA | 165-179 | 7 | 75 |
| 43 | DSGCEGALSPAEREL | 169-183 | 7 | 76 |
| 44 | EGALSPAERELLDFS | 173-187 | 7 | 77 |
| 45 | SPAERELLDFSSWLGGY | 177-193 | 7 | 78 |

Peptides were combined in pools of 6 or 7 peptides/pool (the resulting 45 peptide sequences and 7 pools are detailed in table 5), and pulsed onto autologous dendritic cells (DCs). Following 4 stimulation cycles, donor #1 PBMC cell lines were assayed for proliferation by using a 3H-thymidine incorporation assay and for IFN-γ synthesis by ELISA.

A number of positive peptide pools were identified, with 21 and 7 cells lines exhibited stimulation index (S.I.)>3 and S.I.>5, respectively (Stimulation index reflects the ratio of activity from T cells incubated with DC pulsed with relevant vs. irrelevant peptide or protein).

All positive 21 lines were further re-stimulated with individual peptides. One line, designated 3H8, showed a specific reactivity to peptide #21 (SEQ ID NO:54).

To map the particular epitope within peptide 21 (SEQ ID NO:54) and recognised by the T-cells of donor #1, T-Cell clones ere individualized from the T-cell lines. For this purpose, the line 3H8 was re-stimulated on antigen expanded using polyclonal activator PHA, and cloned on PHA. Clones were then tested for peptide stimulation in IFN-γ ELSA assays.

Several clones from line 3H8 were shown to recognize peptide 21 (SEQ ID NO:54). Clones generated from this 3H8 line recognised peptide but failed to recognise E. coli-derived NS1-CASB7439 protein. Therefore a similar in vitro priming procedure with a new donor has been undertaken to generate T-clones able to recognise the whole CASB7439 protein presented by APC's.

In Vitro Priming of Donor #2

In vitro priming experiments were preformed with the PBMC from an additional donor #2 in similar experimental condition as donor #1. In brief, PBMC were stimulated with autologous DC pulsed with the 7 pools of 6-7 peptides at a concentration of 250 ng/ml for each peptide. 29 cells lines showed reactivity to pooled peptides, and were further assayed on individual peptides (at 250 ng/ml) and on E. coli-derived NS1-CASB7439 protein (10 mg/ml).

5 of these lines (lines 3A3, 4C5, 3C9, 4D5, and 4B12) demonstrated specific reactivity to a particular peptide pool and to both an individual peptide derived from that pool and *E. coli*-derived NS1-CASB7439.

Two of the lines, 3A3 and 4C5, have been cloned using PHA. The resulting clones were assayed against DCs pulsed with *E. coli*-derived NS1-CASB7439 fusion protein (2.5 μg/ml) or with irrelevant protein (OspA: 2.5 μg/ml) and assayed for proliferation (3H-Thy) as well as IFN-γ production. 61 clones from the two cell lines were shown to recognise *E. coli*-derived protein, and all of the 61 clones have been also shown to recognise the peptide 16 (SEQ ID NO: 49) from the pool.

These 16 clones were further characterised by demonstrating MHC Class II restriction. CD4+ clones derived from line 3A3 were assayed against DCs pulsed with *E. coli*-derived NS1-CASB7439 protein or irrelevant protein (OspA: 1 μg/ml) in the presence or absence of antibodies (25 μg/ml) to Class I (W632), Class II (HB145), HLA-DR (L243), or HLA-DQw3 (HB144). These T cell clones were shown to be restricted by MHC Class II, and more precisely are not DR DQw3 restricted. Moreover, a preliminary donor mismatch analyses suggest that these clones are likely restricted by HLA-DQ0602.

Specificity of the NS1-CASB7439 fusion protein generated CD4+ T cell activity is further demonstrated: indeed, a line 3A3 clone CD4 response titers out with CASB7439 protein. No response to OspA, an irrelevant protein used as negative control, is observed.

In Vitro Priming of Donor #3

In vitro priming cultures were established from an additional donor using the same pools of 15-mer peptide overlapping 11 amino acids and the same procedures. Four CD4+ lines, including 4A7 and 4E4, demonstrated *E. coli*-derived recombinant protein reactivity that was blocked by antibody to MHC Class II.

Furthermore, CD4+ clones derived from lines 4A7 and 4E4 were assayed against dendritic cells pulsed with *E. coli*-derived NS1-CASB7439 protein or irrelevant protein (OspA: 10 μg/ml), or CASB7439 peptides (250 ng/ml) in the presence or absence of antibodies to Class I (W632:25 μg/ml) or anti-HLA-DR (L243:25 μg/ml). CD4+ clones derived from these lines present a specificity that is different from the clones descried above, as they are HLA-DR restricted. Moreover, 3 other peptides were shown to be recognised by CD4+ T cells (peptides 23 (SEQ ID NO:56), 24 (SEQ ID NO:57), and 25 (SEQ ID NO:58)), the total number recognised peptide that were identified being 5 so far.

Example 11

Immunohistochemical Analysis of CASB7439 on Tumour and Normal Colon Biopsies CASB7439 protein over-expression in colon tumour was verified by immunohistochemistry (IHC) using a CASB7439 specific rabbit polyclonal antibody (Ab CASB7439 #599, 1/50 dilution) directed against an affinity purified CASB7439 α-peptide (SB599 α-peptide, amino acids Ito 14 of CASB7439).

Ab CASB7439 #599 was generated as follows: a rabbit is immunised with SB599 synthetic α-peptide that is conjugated to a carrier protein (LKH). Conjugate is formulated with Freund's adjuvant, and two rabbits are immunised with formulated conjugate. Four weeks after the second immunisation and four weeks after the third immunisation, blood samples are taken. Anti-CASB7439 antibody titers are estimated in the serum by ELISA.

For IHC, paraffin-embedded formalin fixed tissue was sliced into 8 micron sections. Steam heat induced epitope retrieval (SHIER) in 0.1 M sodium citrate buffer (pH 6.0) was used for optimal staining conditions. Sections were incubated with 10% serum/PBS for 5 minutes. Ten micrograms/ml of primary antibody (SB599) was added to each section for 25 min followed by a 25 min incubation with a biotinylated anti-rabbit antibody. Endogenous peroxidase activity was blocked by three 1.5 min incubations with hydrogen peroxidase. The avidin biotin complex/horse radish peroxidase (ABV/HRP) system was used along with DAB chromogen to visualise antigen expression. Slides were counterstained with hematoxylin.

FIGS. 7 and 8 shows IHC results on colon tumour #9476 biospy and colon normal mucosa #9476, respectively. Anti-CASB7439 immunoreactivity was observed at high level in colon cancer and in normal colon at very low level. Anti-CASB7439 immunoreactivity was localised to the cytoplasm and associated with the plasma membrane of the cells.

Example 12

Demonstration of CASB7439 In Vivo Immunogenicity

Besides being highly tumour specific, the second critical criterion for a candidate vaccine evaluation is its immunogenicity. One way of assessing the immunogenicity of a protein is to immunise naïve animals with synthetic peptides derived from the antigen sequence, and which reproduce natural epitopes. The generated anti-peptide antibodies will then tend to recognise the native antigen, therefore, showing a specific immune response can be raised against the candidate vaccine antigen.

Because of the very nature of the immune response, a classical dose range analysis is replaced by repeated immunisations, allowing comparison of antibody titers before immunisation (control), and after cumulative injections.

Two peptides were selected from CASB7439 antigen sequence for their immunogenic potential: peptides spanning from amino-acids 1-14 (peptide 1) and amino-acids 157-172 (peptide 2). Two rabbits were immunised with each peptide, rabbits SB598 and SB599 with peptide 1 and rabbits SB600 and SB601 with peptide 2.

The selected peptides were conjugated to a carrier protein (KLH). Rabbits were intramuscularly immunised with CASB7439 peptide, 3 times at 3 to 4 weeks intervals with 200 μg of conjugate formulated with Freund's adjuvant. Four weeks after the second immunisation (PP) and four weeks after the third immunisation (GP), blood samples were taken, and the CASB7439 specific antibody titers were estimated in the serum by ELISA. Thus, a dose range of 0, 200 and 400 μg of the antigen conjugate is reproduced.

ELISAs were done in triplicate for each immunising peptide and rabbit serum, and performed as follows: 96 well microplates were coated at 4° C. during 16 hours with either 100 ng of CASB7439 peptide or 100 ng of KLH as coating antigens. After 2-hour saturation at 25° C. with BSA (1 mg/ml), serial dilution of the rabbit sera was added for 2 hours at 25° C. (starting at dilution 1/100). Anti rabbit antibody, conjugated with universal-HRP, was then added at dilution 1/1000 for 2 hours at 25° C. as secondary antibody. Plates were washed and OPD (0.4 mg/ml) is added for 30 min at 25° C. Reaction was stopped with H2SO44M, and OD measured at 492 nm.

ELISA results clearly show an antibody immune response against distinct CASB7439 synthetic peptide can be raised in several rabbits in a dose-dependant manner. This suggests CASB7439 candidate antigen is indeed immunogenic and, when properly formulated with adjuvant as a vaccine, CASB7439 vaccine is able to induce a strong and specific antibody immune response.

The invention claimed is:

1. An immunogenic composition comprising (i) adjuvants and (ii) a protein comprising a polypeptide selected from the group consisting of:
   (a) a polypeptide having at least 95% identity to the amino acid sequence set forth in SEQ ID NO:2; and
   (b) a polypeptide fragment of SEQ ID NO:2,
wherein the adjuvants comprise a CpG oligonucleotide and further comprise QS21 or MPL.

2. The immunogenic composition of claim 1 comprising QS21 and MPL.

3. The immunogenic composition of claim 1, wherein the polypeptide fragment comprises at least 10 contiguous amino acids of SEQ ID NO:2.

4. A process for producing an immunogenic composition of claim 1, comprising the steps of combining a protein according to claim 1 and the adjuvants according to claim 1.

5. The process of claim 4, further comprising the step of combining the immunogenic composition with a third adjuvant selected from the group consisting of QS21 or MPL.

6. An immunogenic composition comprising (i) adjuvants and (ii) a protein comprising a polypeptide having at least 95% identity to the amino acid sequence set forth in SEQ ID NO:2, wherein the adjuvants comprise QS21, a CpG oligonucleotide, and MPL.

7. A process for producing an immunogenic composition of claim 6, comprising the steps of combining a protein according to claim 6 and the adjuvants according to claim 6.

8. The process of claim 7, further comprising the step of combining the immunogenic composition with a further adjuvant.

* * * * *